(12) United States Patent
Ingebritson et al.

(10) Patent No.: US 11,992,522 B2
(45) Date of Patent: May 28, 2024

(54) ATTENUATING BACTERIAL VIRULENCE BY ATTENUATING BACTERIAL FOLATE TRANSPORT

(71) Applicant: Boehringer Ingelheim Vetmedica GmbH, Ingelheim am Rhein (DE)

(72) Inventors: Alaina Ingebritson, Hubbard, IA (US); Axel Neubauer, Savannah, MO (US); Hilda Elizabeth Smith, Lelystad (NL); Astrid De Greeff, Lelystad (NL)

(*) Notice: Subject to any disclaimer, the term of this patent is extended or adjusted under 35 U.S.C. 154(b) by 0 days.

(21) Appl. No.: 18/316,499

(22) Filed: May 12, 2023

(65) Prior Publication Data

US 2024/0115687 A1    Apr. 11, 2024

Related U.S. Application Data

(62) Division of application No. 16/348,330, filed as application No. PCT/US2017/061170 on Nov. 10, 2017, now Pat. No. 11,684,663.

(30) Foreign Application Priority Data

Nov. 11, 2016    (EP) .................................... 16198361

(51) Int. Cl.
| | | |
|---|---|---|
| A61K 39/02 | (2006.01) | |
| A61K 39/09 | (2006.01) | |
| C07K 14/315 | (2006.01) | |
| A61K 39/00 | (2006.01) | |

(52) U.S. Cl.
CPC .......... *A61K 39/092* (2013.01); *C07K 14/315* (2013.01); *A61K 2039/522* (2013.01); *A61K 2039/542* (2013.01); *A61K 2039/552* (2013.01)

(58) Field of Classification Search
None
See application file for complete search history.

(56) References Cited

U.S. PATENT DOCUMENTS

| | | |
|---|---|---|
| 6,165,472 A | 12/2000 | Pearson et al. |
| 2010/0136057 A1 | 6/2010 | Smith |

FOREIGN PATENT DOCUMENTS

| | | |
|---|---|---|
| CN | 106085936 A | 11/2016 |
| EP | 1205552 A1 | 5/2002 |
| JP | 2002516606 A | 6/2002 |
| WO | 1998029432 A1 | 7/1998 |
| WO | 2000005378 A2 | 2/2000 |
| WO | 2007045210 A1 | 4/2007 |

OTHER PUBLICATIONS

Smith, Hilde E., et al., "Selection of Virulence-Associated Determinants of Streptococcus suis Serotype 2 by in Vivo Complementation", Infection and Immunity, 69, No. 3, 2001, pp. 1961-1966.
Ames, Tyler D., et al., "A eubacterial riboswitch class that senses the coenzyme tertrahydrofolate", Chemistry & Biology, 17.7, 2010, pp. 681-685.
Weinberg, Zasha, et al., "Comparative genomics reveals 104 candidate structured RNAs from bacteria, archaea, and their metagenomes", Genome Biology, 11.3, 2010, p. R31.
Eudes, Aymerick, et al., "Identificatoin of genes encoding the folate-and thiamine-binding membrane proteins in Firmicutes", Journal of Bacteriology, 190.22, 2008, pp. 7591-7594.
Xu, Ke, et al., "Crystal structure of a folate energy-coupling factor transporter from Lactobacillus brevis", Nature, 497.6448, 2013, pp. 266-271.
Lasry, Inbal, et al., "A novel loss-of-function mutation in the proton-coupled folate transporter from a patient with hereditary folate malabsorption reveals that Arg 113 is crucial for function", Blood, 112.5, 2008, pp. 2055-2061.
De Greeff, Astrid, et al., "A naturally occurring nucleotide polymorphism in the orf2/folc promoter is associated with *Streptococcus suis* virulence", BMC Microbiology, 14.1, 2014, p. 264.
Ahrweiler, P.M. and Carl Frieden, "Construction of a fol mutant strain of *Escherichia coli* for use of dihydrofolate reductase mutagenesis experiments", Journal of Bacteriology, 170, No. 7, 1988, pp. 3301-3304.
Qin Zhao et al., "Structures of FoIT in substrate-bound and substrate-released conformations reveal a gating mechanism for ECF transporters", Nature Communications, 2015, vol. 6, No. 7661.
Zhao, Qin, et al. "Structures of FoIT in substrate-bound and substrate-released conformations reveal a gating mechanism for ECF transporters." Nature communications 6.1 (2015): 7661.

*Primary Examiner* — Jennifer E Graser
(74) *Attorney, Agent, or Firm* — Suzanne Seavello Shope

(57) ABSTRACT

The invention relates to bacterial infections, vaccines directed against those infections and bacterial vaccines. More particularly, the invention relates to vaccines directed against *Streptococcus* infections in pigs. The invention provides a ΔFolT mutant of a bacterium having reduced capacity to transport folate, wherein said capacity has been reduced by functionally deleting folate transporter (FolT) function. The invention also provides a method to reduce virulence of a bacterium comprising reducing the capacity of said bacterium to transport folate.

14 Claims, 17 Drawing Sheets

Figure 1:
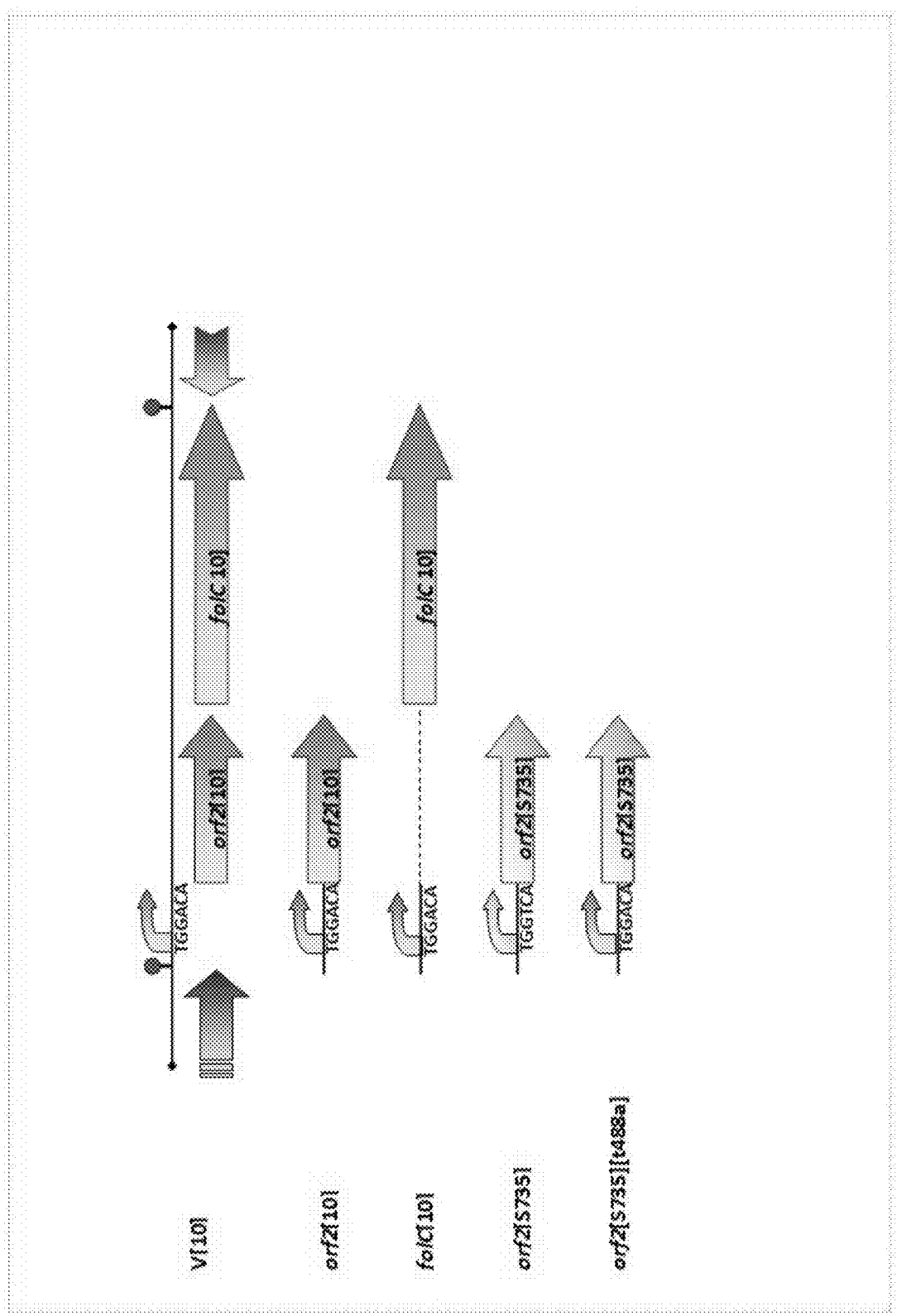
Figure 2:
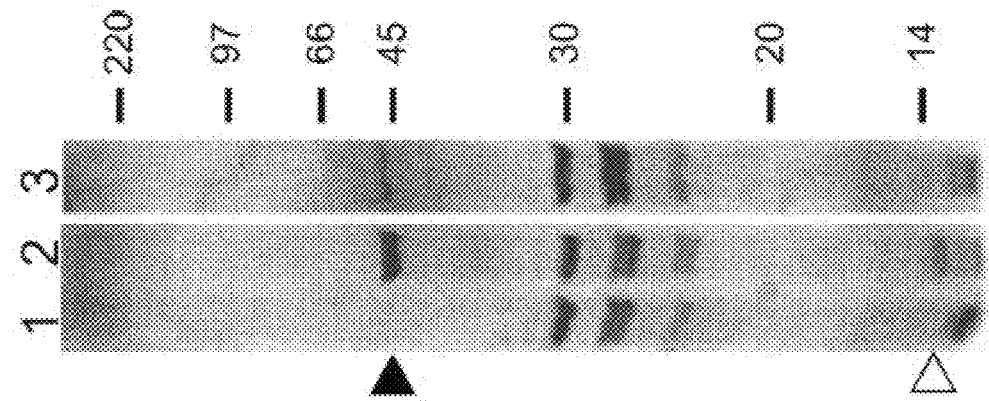

Specification includes a Sequence Listing.

Fig. 4

Figure 17. Mortality rate (CBS 140425)

ATTENUATING BACTERIAL VIRULENCE BY ATTENUATING BACTERIAL FOLATE TRANSPORT

CROSS-REFERENCE TO RELATED APPLICATIONS

This application is a divisional of U.S. patent application Ser. No. 16/348,330, which claims the benefit of International Application No. PCT/US2017/061170, filed Nov. 10, 2017, which claims the benefit of European Application No. 16198361.4, filed Nov. 11, 2016, the entire contents of which are hereby incorporated by reference herein.

SEQUENCE LISTING

The instant application contains a Sequence Listing which has been submitted electronically in XML file format and is hereby incorporated by reference in its entirety. Said XML copy, created on Apr. 25, 2023, is named 02-0481-US-2_SL.xml and is 32,541 bytes in size.

TECHNICAL FIELD

The invention relates to bacterial strains, drugs directed against bacterial infections and bacterial vaccines. More particularly, the invention relates to vaccines directed against *Streptococcus* infections in pigs.

BACKGROUND

Plants, fungi, certain protists, and most bacteria make folate (Vitamin B9) de novo, starting from GTP and chorismate, but higher animals lack key enzymes of the synthetic pathway and so require dietary folate. Folates are crucial to health, and antifolate drugs are widely used in cancer chemotherapy and as antimicrobials. For these reasons, folate synthesis and salvage pathways have been extensively characterized in model organisms, and the folate synthesis pathway in both bacteria and plants has been engineered in order to boost the folate content of foods. Tetrahydrofolate is an essential cofactor for many biosynthetic enzymes. It acts as a carrier of one-carbon units in the syntheses of such critical metabolites as methionine, purines, glycine, pantothenate, and thymidylate. For example, the enzyme ketopantoate hydroxymethyl transferase, encoded by the pang gene, requires a tetrahydrofolate cofactor to synthesize precursors of pantothenate. As tetrahydrofolate is synthesized de novo in bacteria, inhibition of its synthesis kills cells. Indeed, two very effective antibiotics, sulfonamide and trimethoprim, kill bacterial cells by blocking tetrahydrofolate production. These two antibiotics, which are often used in combination with each other, are commonly prescribed for the treatment of urinary tract infections, enteric infections such as shigellosis, and respiratory tract infections. The success of these drugs is indicative of the vulnerability of many pathogenic bacteria to inhibitors of tetrahydrofolate synthesis. Bacteria have a multiple step pathway for the synthesis of the tetrahydrofolate cofactor. In one branch of the pathway, the metabolites chorismate and glutamine are substrates for aminodeoxychorismate synthase, encoded by the *B. subtilis* genes, pabA and pabB, which produces 4-amino 4-deoxychorismate. Aminodeoxychorismate lyase, encoded by *B. subtilis* pabC, then converts 4-amino 4-deoxychorismate to para-aminobenzoic acid (PABA), an important precursor. In another branch, a number of enzymes, including those encoded by *B. subtilis* mtrA, folA, and folK, produce the precursor 2-amino-4-hydroxy-6-hydroxy methyl-7, 8-dihydroxpteridine diphosphate. This precursor and PABA are substrates for dihydropteroate synthetase, encoded by the *B. subtilis* sul gene (homologous to the *E. coli* dhps and folP genes), which produces dihydropteroate. Sulfonamides, such as sulfamethoxazole, are competitive inhibitors of dihydropteroate synthase. Dihydropteroate is modified by the bifunctional enzyme encoded by *B. subtilis* folC to produce dihydrofolate. Finally, DHFR (dihydrofolate reductase), encoded by *B. subtilis* dfrA, modifies this dihydrofolate to generate the end product tetrahydrofolate. Trimethoprim is a competitive inhibitor of bacterial DHFRs. This selectivity is critical, as eukaryotic DHFRs are unimpeded by the antibiotic. Folate is most probably essential for all sequenced bacteria except *M. hyopneumoniae*. However, not all bacteria synthesize folate de novo but instead rely on an external supply. To predict the absence of the de novo synthesis pathway, the HPPK (FolK) and DHPS (FolP) proteins are used as signature proteins. Many bacteria lack homologs of both these genes and so almost certainly rely on reducing and glutamylating intact folates taken up from the environment. These are mainly host-associated bacteria such as *Mycoplasma* or *Treponema* or organisms that live in folate-rich environments such as Lactobacilli.

*Streptococcus* species, of which there are a large variety causing infections in domestic animals and man, are often grouped according to Lancefield's groups. Typing according to Lancefield occurs on the basis of serological determinants or antigens that are among others present in the capsule of the bacterium and allows for only an approximate determination, often bacteria from a different group show cross reactivity with each other, while other Streptococci cannot be assigned a group determinant at all. Within groups, further differentiation is often possible on the basis of serotyping; these serotypes further contribute to the large antigenic variability of Streptococci, a fact that creates an array of difficulties within diagnosis of and vaccination against streptococcal infections. Lancefield group A *Streptococcus* (GAS, *Streptococcus pyogenes*), are common with children, causing nasopharyngeal infections and complications thereof. Group B streptococci (GBS) constitute a major cause of bacterial sepsis and meningitis among human neonates and are emerging as significant neonatal pathogens in developing countries. Lancefield group B *Streptococcus* (GBS) are also found to be associated with cattle, causing mastitis. Lancefield group C infections, such as those with *S. equi, S. zooepidemicus, S. dysgalactiae*, and others are mainly seen with horse, cattle and pigs. Lancefield group D (*S. bovis*) infections are found with all mammals and some birds, sometimes resulting in endocarditis or septicaemia. Lancefield groups E, G, L, P, U and V (*S. porcinus, S. canis, S. dysgalactiae*) are found with various hosts, causing neonatal infections, nasopharyngeal infections or mastitis. Within Lancefield groups R, S, and T, (and with ungrouped types) *S. suis* is found, an important cause of meningitis, septicemia, arthritis and sudden death in young pigs. Incidentally, it can also cause meningitis in man. Ungrouped *Streptococcus* species, such as *S. mutans*, causing caries with humans, *S. uberis*, causing mastitis in cattle, and *S. pneumonia*, causing invasive diseases, such as pneumonia, bacteraemia, and meningitis.

*Streptococcus suis* is a zoonotic pathogen that is ubiquitously present among swine populations in the pig industry. Thirty-three capsular serotypes have been described to date [1] of which serotypes 1, 2, 7, 9 and 14 are frequently isolated from diseased pigs in Europe [2]. Strain virulence differs between and within serotypes: within serotype 2, virulent, avirulent as well as weakly virulent isolates have been isolated that can be discriminated based on the expression of virulence markers, muramidase released protein (MRP) and extracellular factor (EF) [3] and suilysin [4,5]. Nasopharyngeal carriage of S. suis in adult pigs is asymptomatic, whereas in young piglets this increases susceptibility to S. suis invasive disease, leading to meningitis, arthritis and serositis, and high rates of mortality. In Western countries humans occupationally exposed to pigs or uncooked pork might also become infected by S. suis although the incidence is very low. Invasive S. suis infection of humans gives similar clinical signs as in pigs; patients often suffer from remaining deafness after recovery [6]. In Southeast Asia, S. suis, in particular of serotype 2, is considered an emerging pathogen for humans, and is recognized as leading cause of bacterial meningitis [7-10]. In Southeast Asia, clinical signs of human infections with S. suis are reported to be more severe compared to other parts of the world, with patients developing toxic shock-like syndrome, sepsis and meningitis. Little is known about the pathogenesis of the disease caused by S. suis. Various bacterial components, such as extracellular and cell membrane associated proteins, play a role in the pathogenesis. Moreover, it has been shown that the capsule is an important virulence factor by enabling these microorganisms to resist phagocytosis. Current strategies to prevent S. suis infections in pigs include antibiotic treatment of diseased pigs, combined with vaccination strategies with autovaccines [11]. Although auto-vaccination with bacterin vaccines against serotype 2 has shown to be able to reduce clinical outbreaks on farms, the same is not true for serotype 9, where autovaccination does not seem to protect efficiently [12,13]. Besides the fact that bacterin vaccines are less effective against serotype 9 infections, they can only protect against the serotype present in the vaccine. As mentioned before however, several serotypes can cause disease, thus autovaccines are a temporarily solution to a clinical outbreak. For a long-term solution against S. suis infections, vaccines are required that protect broadly against all (pathogenic) serotypes. A lot of research has been done to find suitable vaccine candidates, however, no cross protective vaccine is available yet.

THE INVENTION

The invention provides a method to produce a bacterium, preferably for use in a vaccine, preferably for use in a vaccine to generate protection against a bacterial infection, comprising selecting a parent bacterial strain generally capable of folate transport and folate synthesis and selecting a bacterium from that parent strain for having a modification such as a mutation, deletion or insertion in the DNA region encoding for the folate substrate binding protein (in *Streptococcus suis* known as the folT gene) of said bacterium and selecting said bacterium for the capacity to grow to similar rates as said parent strain in vitro but to grow to reduced rates compared with said parent strain in vivo. The invention also provides a method to produce a bacterium, preferably for use in a vaccine, preferably a vaccine for use to generate protection against a bacterial infection, comprising selecting a parent bacterial strain generally capable of folate transport and folate synthesis and transforming, preferably by recombinant means, a bacterium from that parent strain by providing it with a modification such as a mutation, deletion or insertion in the DNA region encoding for the folate substrate binding protein (in *Streptococcus suis* known as the folT gene) of said bacterium and selecting said bacterium for the capacity to grow to similar rates as said parent strain in vitro but to grow to reduced rates compared with said parent strain in vivo. The invention also provides a bacterium, a bacterial culture obtainable or obtained with a method of selecting or transforming according to the invention. It is preferred that said bacterium as provided herein is classifiable as a Firmicutes, preferably a *Streptococcus*, more preferably a *Streptococcus suis*. The invention also provides a composition comprising a bacterium or a culture of a bacterium capable to grow to similar rates as said parent strain in vitro but growing to reduced rates compared with said parent strain in vivo. It is also provided to use such a composition for the production of a vaccine. Preferably, such a vaccine comprises a bacterium or a culture of a bacterium capable to grow to similar rates as said parent strain in vitro but growing to reduced rates compared with said parent strain in vivo.

The invention also provides a method to reduce (attenuate) virulence of a bacterium, said bacterium preferably capable of de novo folate synthesis, comprising reducing the capacity of said bacterium to transport folate. The inventors provide a bacterium, herein generally called ΔFolT mutant, in particular a *Streptococcus suis* strain is herein provided, wherein said capacity has been strongly reduced by functionally deleting folate transporter (Farr) function. This bacterium, as provided herein, still has the capacity to produce folate for its own use by applying its de novo folate synthesis pathways. Having these synthesis pathways intact leaves its capacity to in vitro growth (in culture) unaffected, surprisingly it was however shown that its growth and virulence in the host (in vivo) was strongly reduced. Such a bacterial strain that grows well in vitro but in vivo grows less than its parent strain and has associated strongly reduced virulence in vivo is very useful as a vaccine strain. Such a strain or mutant as provided by the invention is, on the one hand, essentially unaffected in folate synthesis and thus able to be grown to high titres and thereby relatively easy and inexpensive to produce, while on the other hand it is, due to its reduced growth and reduced virulence in its host as compared to its parent strain, relatively innocuous after in vivo application, making it extremely useful as a vaccine directed against a bacterial infection.

A prototype ΔFolT mutant strain provided with a modification in the DNA region encoding for the folate substrate binding protein (in *Streptococcus suis* known as the folT gene) and having similar growth in culture (in vitro) as its parent strain but having reduced growth in vivo as opposed to its parent strain, has been deposited as "CBS 140425 *Streptococcus suis* ΔFolT mutant" at the Centraalbureau voor Schimmelcultures for the purpose of patent procedure under the Regulations of the Budapest Treaty at Aug. 19, 2015. Another prototype ΔFolT mutant strain provided with a modification in the DNA region encoding for the folate substrate binding protein (in *Streptococcus suis* known as the folT gene) and having similar growth in culture (in vitro) as its parent strain but having reduced growth in vivo as opposed to its parent strain, has been deposited as "CBS 143192 *Streptococcus suis* ΔFolT2 mutant" at the Westerdijk Fungal Biodiversity Institute at Aug. 25, 2017.

The capacity of de novo folate synthesis of a bacterium can be easily tested by methods known in the art, such as by testing growth of the bacterium in culture media without folate, in comparison with culture media provided with folate, or other methods reviewed in *BMC Genomics* 2007, 8:245 (doi:10.1186/1471-2164-8-245, incorporated herein by reference). Most bacteria have at least two independent pathways to acquire tetrahydrofolate: one following the classical folate synthesis pathway, and one fast method using the folate transporter to import folate. In vitro it is now herein provided that there are sufficient nutrients and energy available using the classical synthesis pathway. Not wishing to be bound by theory but offering a possible explanation of the effects found by the inventors, in vivo, when there may be lack of nutrients and thus energy, it may be a lot harder to invest in THF production following the classical pathway. The alternative to import folate is apparently chosen then. Based on ongoing experiments, we postulate that expression of folT is a burden for the bacterium, probably due to its high hydrophobicity. In vitro, increased expression of folT decreases growth rate. This is probably the reason why expression of folT is so strictly regulated by the presence of its riboswitch. It should only be expressed when there is absolute necessity. In conclusion, there seems to be a balance between nutrient availability and THF requirement versus the burden of protein expression. It is now found herein by the inventors that this balance tips in vitro to one side, increased de novo folate synthesis, and in vivo to the other side, increased folate transport. Surprisingly, attenuating (reducing) folate transport in the in vivo route, preferably knocking out folate transport in the in vivo route by functionally deleting folate transporter function, reduces bacterial virulence in the host and not in culture. In a preferred embodiment, the invention provides a ΔFolT mutant of a bacterium having reduced capacity to transport folate, wherein said capacity has been reduced by functionally deleting folate transporter (FoiT) function. In particular, the inventors herein provide a method to attenuate (reduce) expression and/or function of the folate substrate binding protein (FolT) of said bacterium, in particular by providing a mutation, deletion or insertion in the folT gene of said bacterium or in the promotor of said gene. Such a mutation, deletion or insertion can be detected by PCR and/or sequence analysis, as known in the art. In a particular embodiment of the invention, a method is provided to knockout the folT gene, attenuating a bacterium, such as *S. suis*, considerably, and making it suitable for in vivo use as a vaccine strain that still may be cultured easily in vitro. In another embodiment, the invention provides a method wherein said virulence is attenuated by providing a mutation, deletion or insertion in the DNA of said bacterium encoding a transmembrane region of folate substrate binding protein FolT, preferably leaving immunogenicity of Foil essentially intact, most preferably leaving the hydrophilic protein domains of Foil essentially intact. In another embodiment, the invention provides a method wherein said virulence is attenuated by providing a mutation, deletion or insertion in the Foil encoding DNA region of said bacterium encoding a region crucial for substrate binding, said region in *S. suis* characterized by a peptide domain having a stretch of amino acids FYRKP. It is preferred to mutate at least the arginine (R) in the FYRKP stretch to abolish folate binding. In a preferred method of the invention the bacterium is classifiable as a Firmicutes, preferably a *Streptococcus*, more preferably a *Streptococcus suis*. It is preferred that a ΔFolT mutant according to the invention is having the capacity to synthesize folate; having these synthesis pathways intact leaves its capacity to in vitro growth (in culture) unaffected, however, strongly reduces its virulence in a host (in vivo), making it very suitable for vaccine use. It is preferred that said ΔFolT mutant according to the invention is having attenuated (reduced or hampered) expression of FolT, for example characterised by reduced expression of Foil per se or by expression of Foil variant protein with reduced molecular weight, such as can for example be tested by testing Foil specific nucleotide constructs of said mutant in in vitro transcription/translation studies as described in the experimental section herein. In one particular preferred embodiment, the invention provides a ΔFolT mutant according to the invention deposited as "CBS 140425 *Streptococcus suis* ΔFolT mutant" at the Centraalbureau voor Schimmelcultures at Aug. 19, 2015. In another particular preferred embodiment, the invention provides a ΔFolT mutant according to the invention deposited as "CBS 143192 *Streptococcus suis* ΔFolT2 mutant" at the Westerdijk Fungal Biodiversity Institute at Aug. 25, 2017.

In another particular preferred embodiment, the invention provides a ΔFolT mutant strain according to the invention. Any of these deposits may also be used to provide ΔFolT mutant nucleotide constructs as control constructs in expression studies with further bacterial ΔFolT mutants to study expression of Foil variant gene expression or Foil variant protein expression. Any of these deposits may also be used to provide a ΔFolT mutant bacterial culture, or a composition comprising ΔFolT mutant bacterial culture according to the invention. The invention herewith also provides a bacterium with attenuated virulence obtainable or obtained with a method provided herein, and a culture of such a bacterium. Also provided is a composition that comprises a ΔFolT mutant bacterium or a ΔFolT mutant culture according to the invention, and use of such a composition for the production of a vaccine. The invention also provides a vaccine comprising a ΔFolT mutant bacterium or a ΔFolT mutant culture as provided herein. In a preferred embodiment, provided is a *Streptococcus* vaccine strain or vaccine, including a ΔFolT mutant capable of expressing a non-*Streptococcus* protein. Such a vector-*Streptococcus* ΔFolT mutant vaccine strain allows, when used in a vaccine, protection against pathogens other than *Streptococcus*. Due to its avirulent character, a *Streptococcus* vaccine strain or ΔFolT mutant as provided herein is well suited to generate specific and long-lasting immune responses, not only against Streptococcal antigens, but also against other antigens expressed by the strain. Specifically, antigens derived from another pathogen are now expressed without the detrimental effects of the antigen or pathogen, which would otherwise be harmful to the host. An example of such a vector is a *Streptococcus* vaccine strain or ΔFolT mutant wherein the antigen is derived from a pathogen, such as *Actinobacillus pleuropneumonia, Bordetella, Pasteurella, E. coli, Salmonella, Campylobacter, Serpulina* and others. Also provided is a vaccine including a *Streptococcus* vaccine strain or ΔFolT mutant and a pharmaceutically acceptable carrier or adjuvant. Carriers or adjuvants are well known in the art; examples are phosphate buffered saline, physiological salt solutions, (double-) oil-in-water emulsions, aluminumhydroxide, Specol, block- or co-polymers, and others. A vaccine according to the invention can include a vaccine strain either in a killed or live form. For example, a killed vaccine including a strain having (over) expressed a Streptococcal or heterologous antigen or virulence factor is very well suited for eliciting an immune response. In certain embodiments, provided is a vaccine wherein the strain is living, due to its avirulent character; a *Streptococcus* vaccine strain based on a ΔFolT mutant, as provided herein, is well suited to generate specific and long-lasting immune responses. Also provided is a method for controlling or eradicating a Streptococcal disease in a population, the method comprising vaccinating subjects in the population with a ΔFolT mutant vaccine according to the invention. It was provided herein that *S. suis* has an operon that has an important role in pathogenesis and/or virulence of *S. suis*. The operon encodes two genes involved in folate acquisition and processing of folate into tetrahydrofolate. Folate is a general term for a group of water soluble B-vitamins, where folate refers to various tetrahydrofolate derivatives. These derivatives can enter the main folate metabolic cycle, either directly or after initial reduction and methylation to tetrahydrofolate. Folate is essential to all living organisms, both prokaryotes and eukaryotes, making folate metabolism a crucial process. The folT-folC operon seems to form an escape route to acquire folate under folate-restricted conditions, like for example in vivo where the host sequesters folate for its own use. Under these conditions, expression of the folT-folC operon is induced by the riboswitch. When the folate levels drop, tetrahydrofolate will be released from the riboswitch, allowing it to unfold. This allows initiation of translation by the release of the ribosomal binding site. Expression of folT-folC allows *S. suis* to import folate directly by the folate transporter complex, and subsequent process folate into tetrahydrofolate by folC. Since folate is critical for nucleotide synthesis, acquisition of folate has a direct effect on the growth rate of *S. suis*. Decreased growth rates in vivo leads to decreased virulence. By demonstrating that isogenic knockout mutants of folT such as a mutant deposited as CBS 140425 or as CBS 143192 are strongly attenuated and useful as a vaccine, this finding was further supported. The operon is indeed involved in in vivo pathogenesis. The invention herewith now provides such mutants and cultures and compositions and vaccines comprising such a Farr knockout mutant strain having reduced virulence. The invention also provides an immunogenic composition comprising a bacterium having such reduced virulence, and use of such a composition the production of a vaccine, Furthermore, a vaccine comprising a bacterium ΔFolT mutant, such as a mutant deposited as CBS 140425 or as CBS 143192, or a culture or a composition thereof is provided herein. The invention also provides a kit for vaccinating an animal, preferably a pig, against a disease associated with a *Streptococcus suis* infection comprising: a dispenser for administering a vaccine to an animal, preferably a pig; and a ΔFolTmutant strain, such as a mutant deposited as CBS 140425 or as CBS 143192, according to the invention, or culture or composition thereof and optionally an instruction leaflet. To conclude, the invention provides a general method to reduce virulence of a bacterium comprising reducing the capacity of said bacterium to transport folate, the method in particular applicable wherein said bacterium is capable of de novo folate synthesis. The method of the invention as herein provided comprises selecting a bacterium having a functional folate substrate binding protein and then attenuating expression and/or function of the folate substrate binding protein (Farr) of said bacterium, in particular wherein said virulence is attenuated by providing a mutation, deletion or insertion in the folT gene of said bacterium, for example by providing a mutation, deletion or insertion in the DNA of said bacterium encoding the promotor of the folT gene. In certain embodiments of the invention it is preferred to attenuate said virulence by providing a mutation, deletion or insertion in the DNA of said bacterium encoding a transmembrane region of folate substrate binding protein Farr. In another particular embodiment, said virulence is attenuated by providing a mutation, deletion or insertion in the Farr encoding DNA region of said bacterium encoding a region crucial for substrate binding. Also, a method to obtain an immunogenic composition or vaccine is provided herein that is applicable to a bacterium wherein said bacterium is a Firmicutes, preferably a *Streptococcus*, more preferably a *Streptococcus suis*, more preferably a ΔFolT mutant deposited as "CBS 140425 *Streptococcus suis* ΔFolT mutant" at the Centraal bureau voor Schimmelcultures at Aug. 19, 2015, most preferably a ΔFolT mutant deposited as "CBS 143192 *Streptococcus suis* ΔFolT2 mutant" at the Westerdijk Fungal Biodiversity Institute at Aug. 25, 2017. The invention also provides a bacterium with attenuated virulence obtainable or obtained with a method to attenuate virulence by attenuating Farr expression according to the invention, and provides a culture of a such a bacterium, and a composition comprising such a bacterium having reduced virulence or a culture of such a bacterium having reduced virulence, and an immunogenic composition comprising a bacterium having reduced virulence or a culture of a bacterium having reduced virulence, and provides use of culture such a bacterium having attenuated Foil expression or a composition of a bacterial culture having attenuated Foil expression for the production of a vaccine. The invention also provides a vaccine comprising a bacterium having attenuated Foil expression or a culture of a bacterium having attenuated Foil expression or comprising a composition of a culture of a bacterium having attenuated Foil expression. The invention also provides a kit for vaccinating an animal, against a disease associated with a particular bacterium having Foil expression infection comprising a) a dispenser for administering a vaccine to an animal, and b) an isogenic knock out strain (mutant) of said particular bacterium having attenuated Foil expression, or a culture of an isogenic knock out strain of said particular bacterium having attenuated Foil expression, or a composition comprising a culture of an isogenic knock out strain of said particular bacterium having attenuated Foil expression, and c) optionally an instruction leaflet. Such a particular bacterium, according to the invention provided with attenuated Foil expression and having reduced capacity to transport folate, wherein said capacity has been reduced by functionally deleting folate transporter (Foil) function, in general have good growth characteristics in culture media, in particular when a ΔFolT mutant according to the invention is used that has the capacity to synthesize folate; having these synthesis pathways intact leaves its capacity to in vitro growth (in culture) unaffected, however, strongly reduces its virulence in a host (in vivo), making it very suitable for vaccine use.

FIGURE LEGENDS

FIG. 1.

V[10] depicts the clone that was identified using a complementation strategy containing two incomplete ORFs (greyish blue arrows) and a putative operon (purple) containing orf2[10] and folC[10] preceded by the putative promoter of the operon (for clarification only the sequence of the −35 region (TGGACA) of the putative promoter is depicted in the diagram). Constructs were made that contained either orf2[10] or folC[10] (purple) preceded by the putative −35 region of the putative promoter region of the operon (purple). A construct containing orf2 from strain S735 (green) with the −35 region of the putative S735 promoter (TGGTCA) (green) was made. The same construct was mutagenized to contain the −35 region of the putative promoter sequence of strain 10 (TGGACA) (purple) yielding orf2[S735] [t488a].

FIG. 2. In vitro transcription/translation of FolC and ORF2/FolT. In vitro transcription translation of the control construct pCOM1 (lane 1), and constructs pCOM1-V[10] (lane 2), and pCOM1-folc[10] (lane 3). The molecular weight marker is indicated in kDa on the right. FolC expression was detected at the expected weight of 46.8 kDa (closed arrowhead), whereas expression of OR2/FolT was detected at a lower molecular weight, 14 kDa than expected (20.5 kDa) (open arrowhead).

Figure 3:
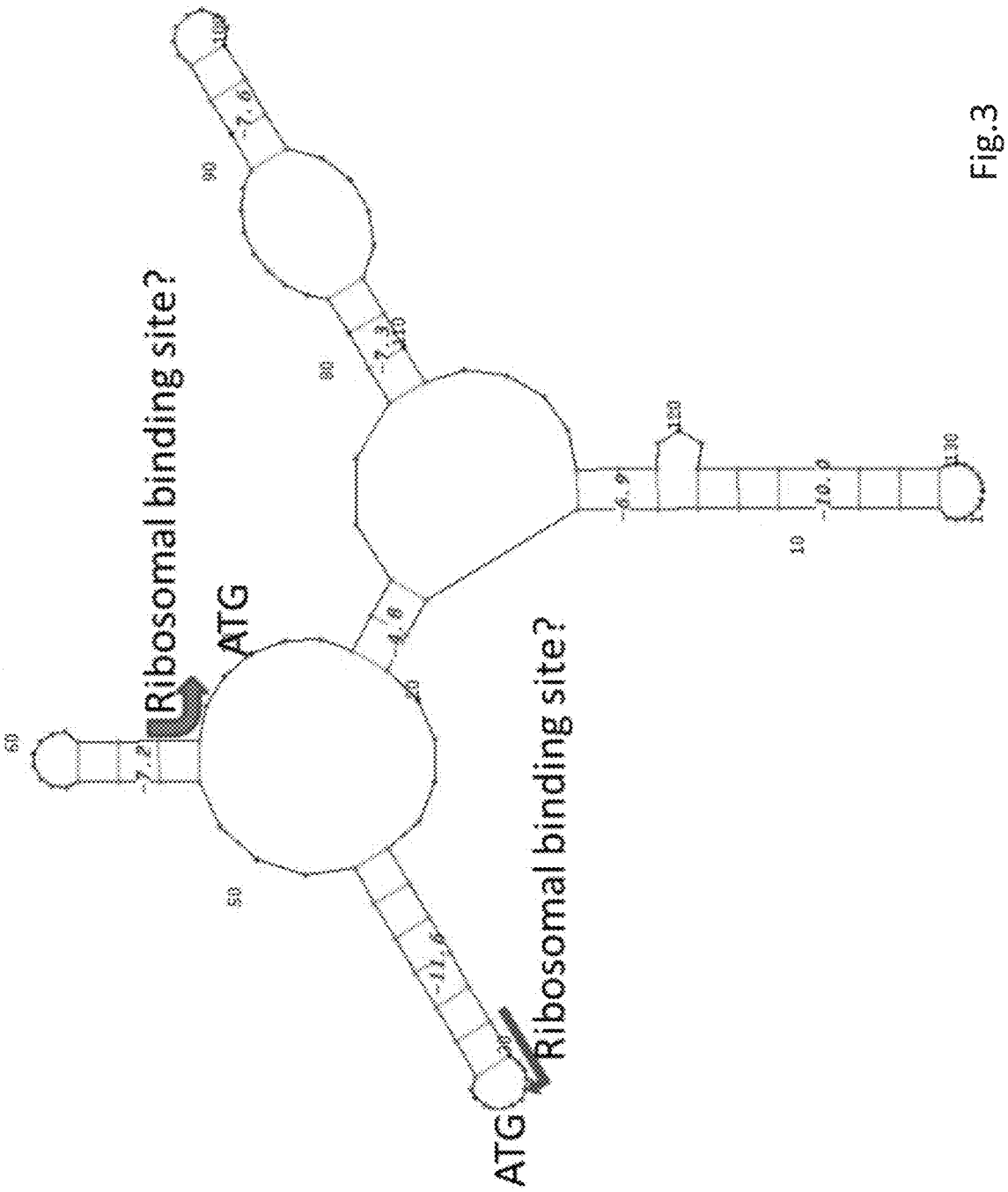

FIG. 3. Predicted riboswitch for tetrahydrofolate using Rfam. Three-dimensional structuring of RNA suggested a riboswitch in which two putative ribosomal binding sites (blue arrows) are inaccessible for ribosomes due to folding.

Figure 4:
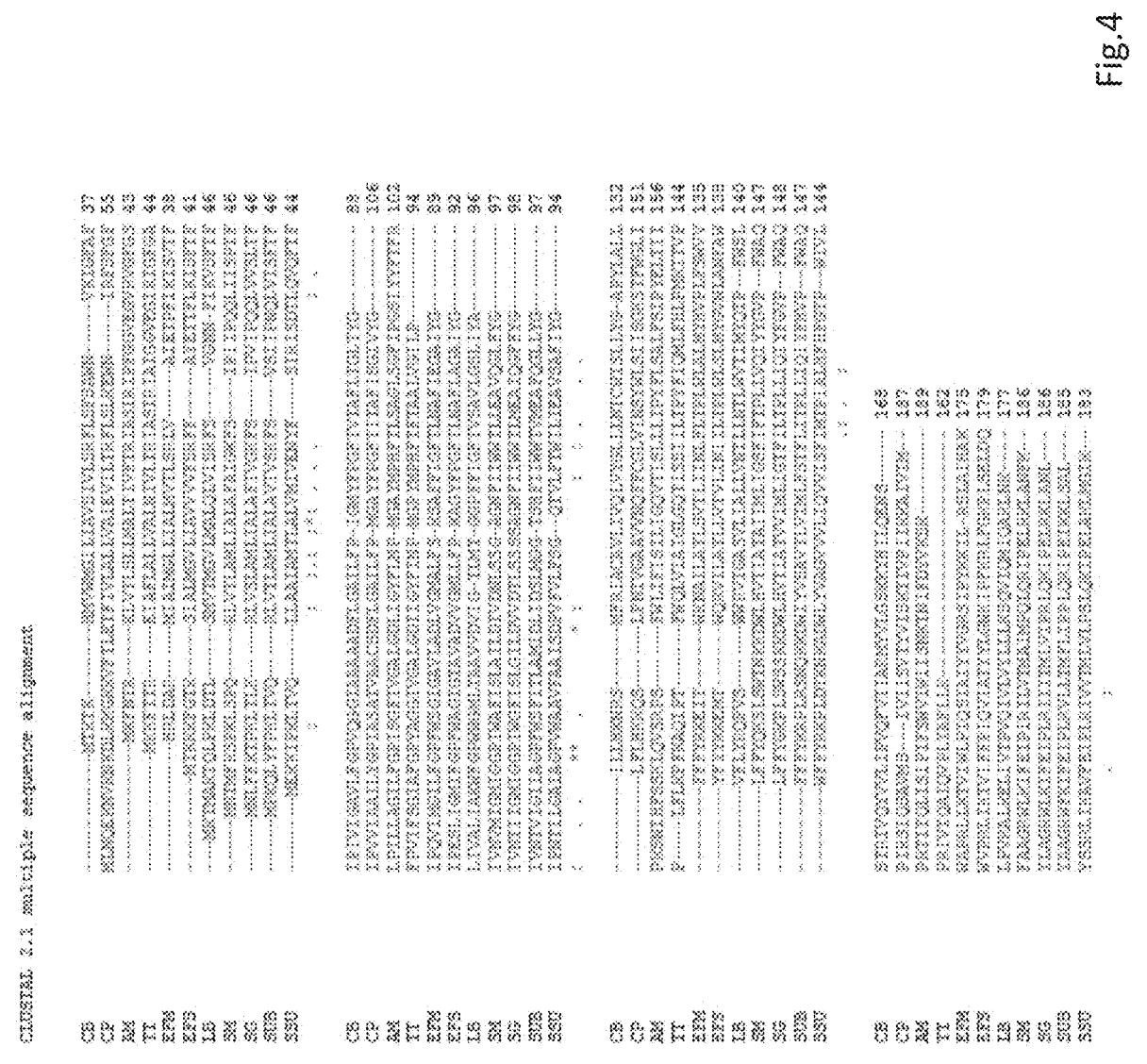

FIG. 4. Clustal W alignment of different FolT sequences. * indicates identical amino acids; : indicates conservation between groups of strongly similar properties; . indicates conservation between groups of weakly similar properties. CB=*Clostridium bolteae*; CP=*Clostridium phytofermentans*; AM=*Alkaliphilus metalliredigens*; TT=*Thermoanaerobacter tengcongensis*; EFM=*Enterococcus faecium*; EFS=*Enterococcus faecalis*; LB=*Lactobacillus brevis*; SM=*Streptococcus mutans*; SG=*Streptococcus gallolyticus*; SUB=*Streptococcus uberis*; SSU=*Streptococcus suis* P1/7.

Red indicates the small and hydrophobic amino acids (including aromatic—Tyr); blue indicates acidic amino acids; Magenta indicates basic amino acids and green indicates hydroxyl, sulphydryl, amine and Gly.

Figure 5:
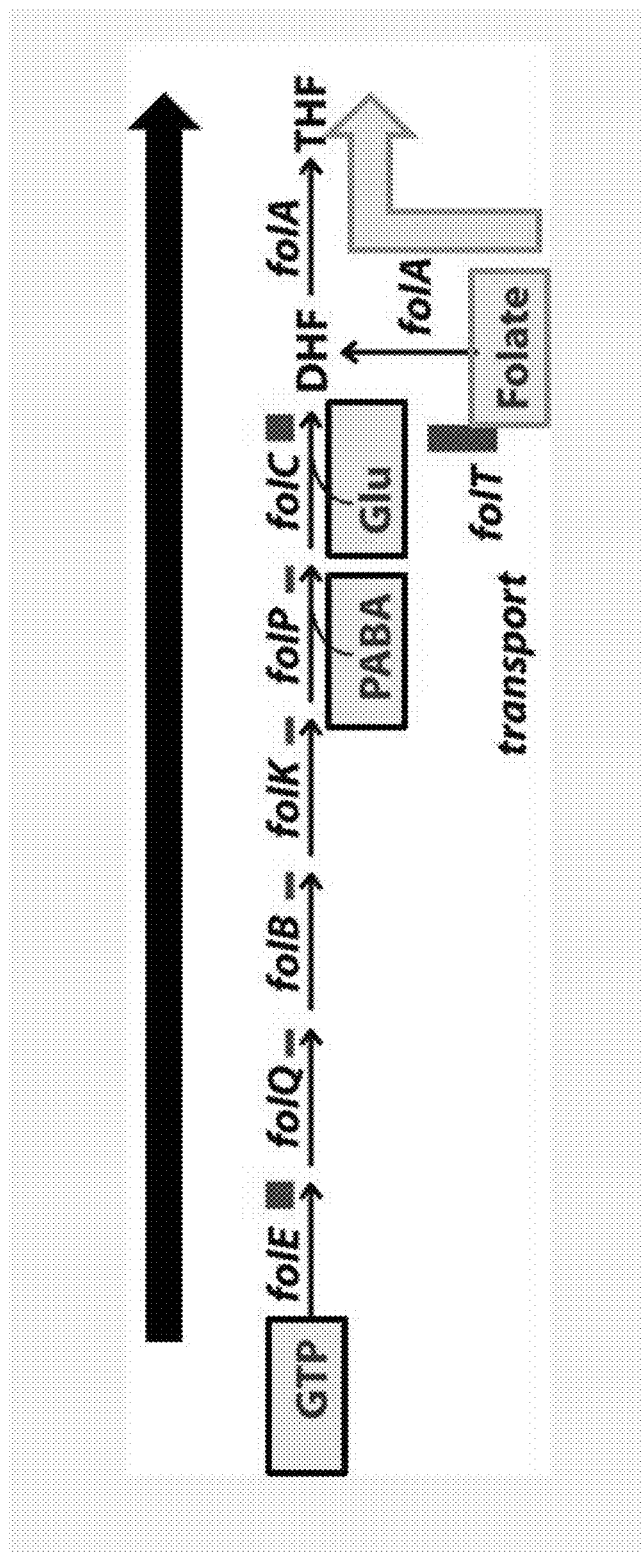

FIG. 5. Folate metabolism in *Streptococcus suis*.

Schematic presentation of the putative folate metabolism of *S. suis*.

Figure 6:
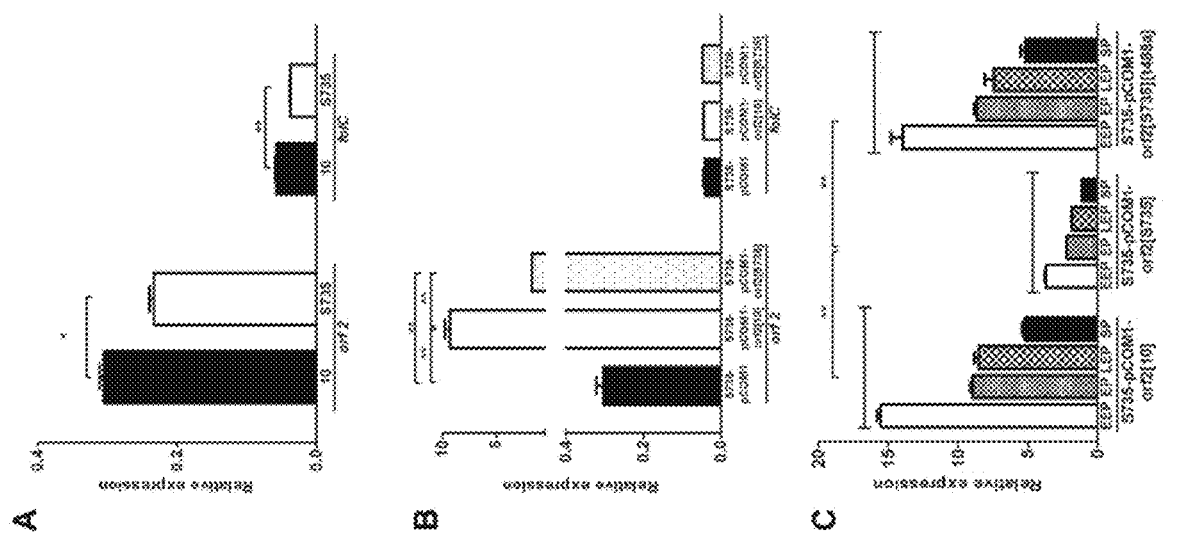

FIG. 6. Expression levels of orf2 and folC in *S. suis* wild-type isolates and mutants.

Expression level of orf2 and folC in *S. suis* wild type isolates strain 10 (black bars) and S735 (white bars) grown exponentially in Todd Hewitt (panel A); and in strain S735 complemented with empty control plasmid pCOM1 (black bars), with orf2[10] (white bars) or with orf2[S735] (hatched bars) grown exponentially in Todd Hewitt (panel B). Expression level of orf2 in S735 complemented with orf2[10], orf2[S735] and orf2[S735] [t488a] after growing in Todd Hewitt until early exponential phase (EEP) (white bars), exponential phase (EP) (small hatched bars), late exponential phase (LEP) (large hatched bars) and stationary phase (SP) (black bars) (panel C). Expression levels were determined using qPCR and expressed as relative expression to housekeeping gene recA. The experiments were performed in triplicate; error bars indicate standard error of the mean. Significance was determined by paired t-tests. *$p<0.05$; **$p<0.01$.

Figure 7:
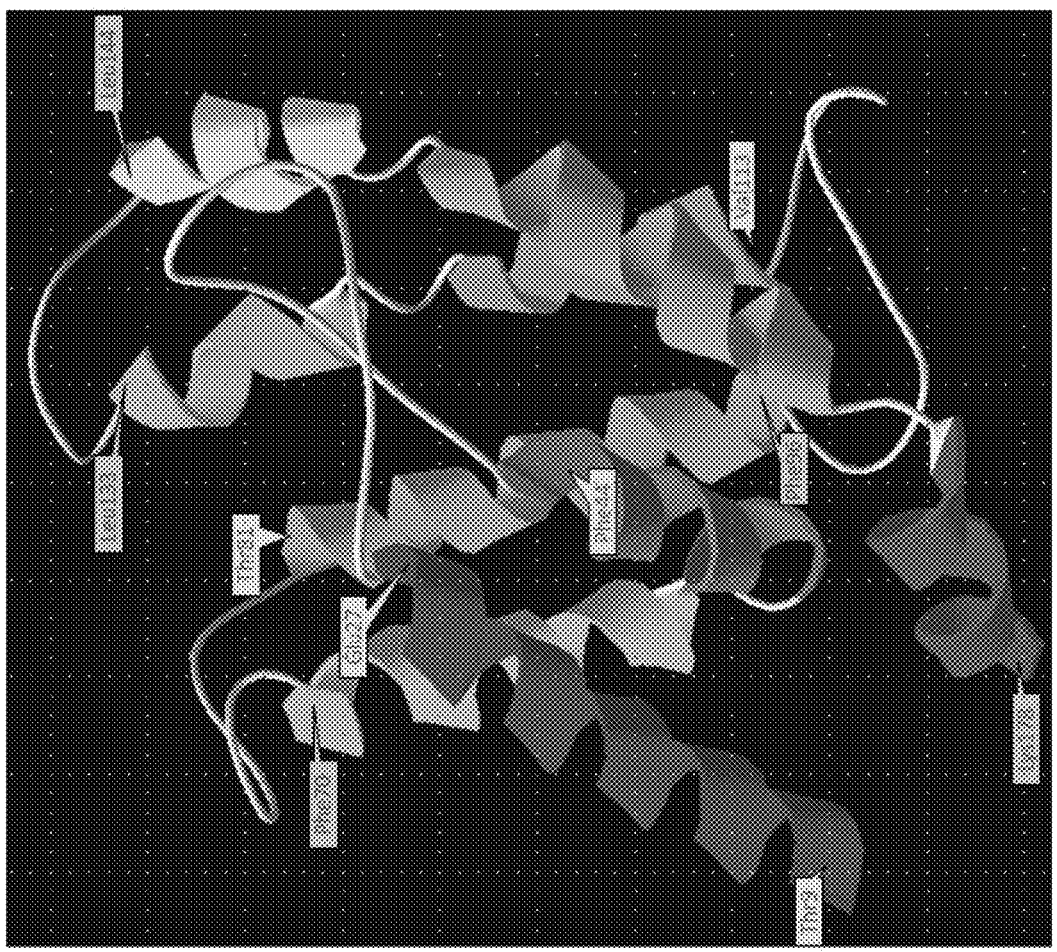

FIG. 7. Predicted 3-dimensional structure for FolT protein of *S. suis*.

Figure 8:
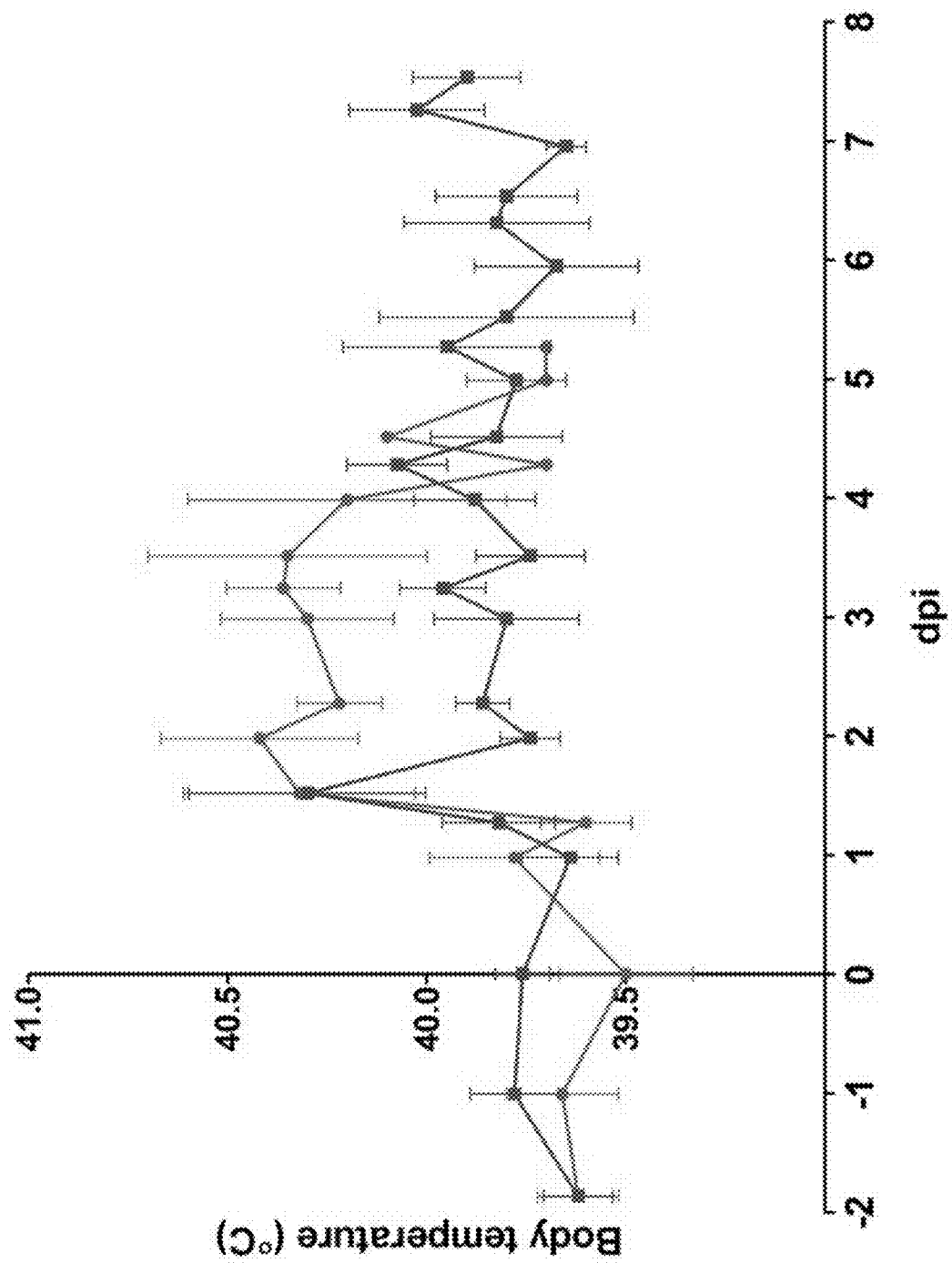

FIG. 8. Body temperature of piglets after *S. suis* infection, experiment 1. Averaged body temperatures of piglets (n=5) either infected with wild type strain 10 (pink) or with strain 10ΔfolT (CBS 140425) are depicted. Error bars indicate standard error of the mean.

Figure 9:
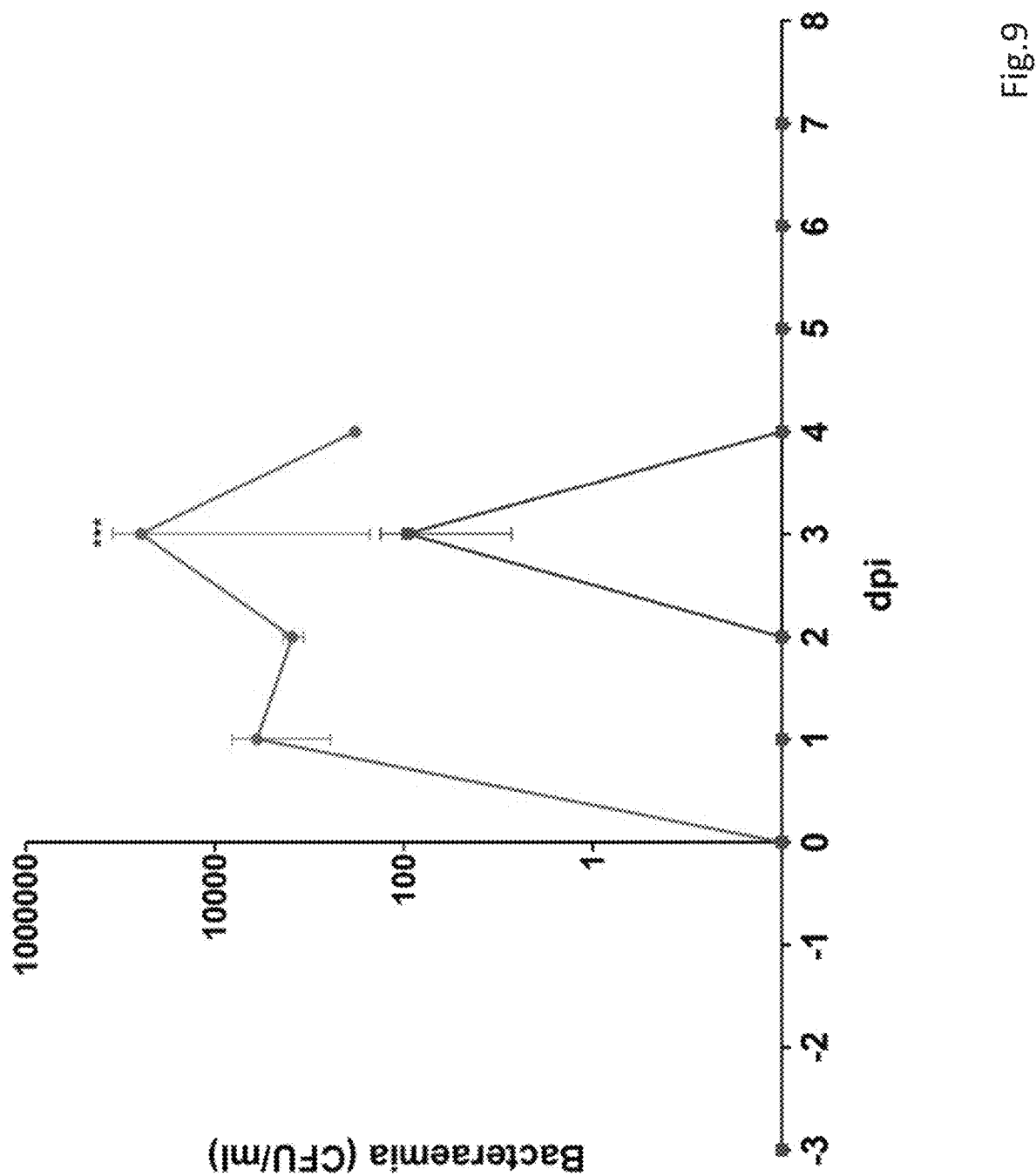

FIG. 9. Bacteraemia of piglets after *S. suis* infection, experiment 1. Averaged bacteraemia of piglets (n=5) either infected with wild type strain 10 (pink) or with strain 10ΔfolT (CBS 140425) (blue) are depicted. Error bars indicate standard error of the mean.

Figure 10:
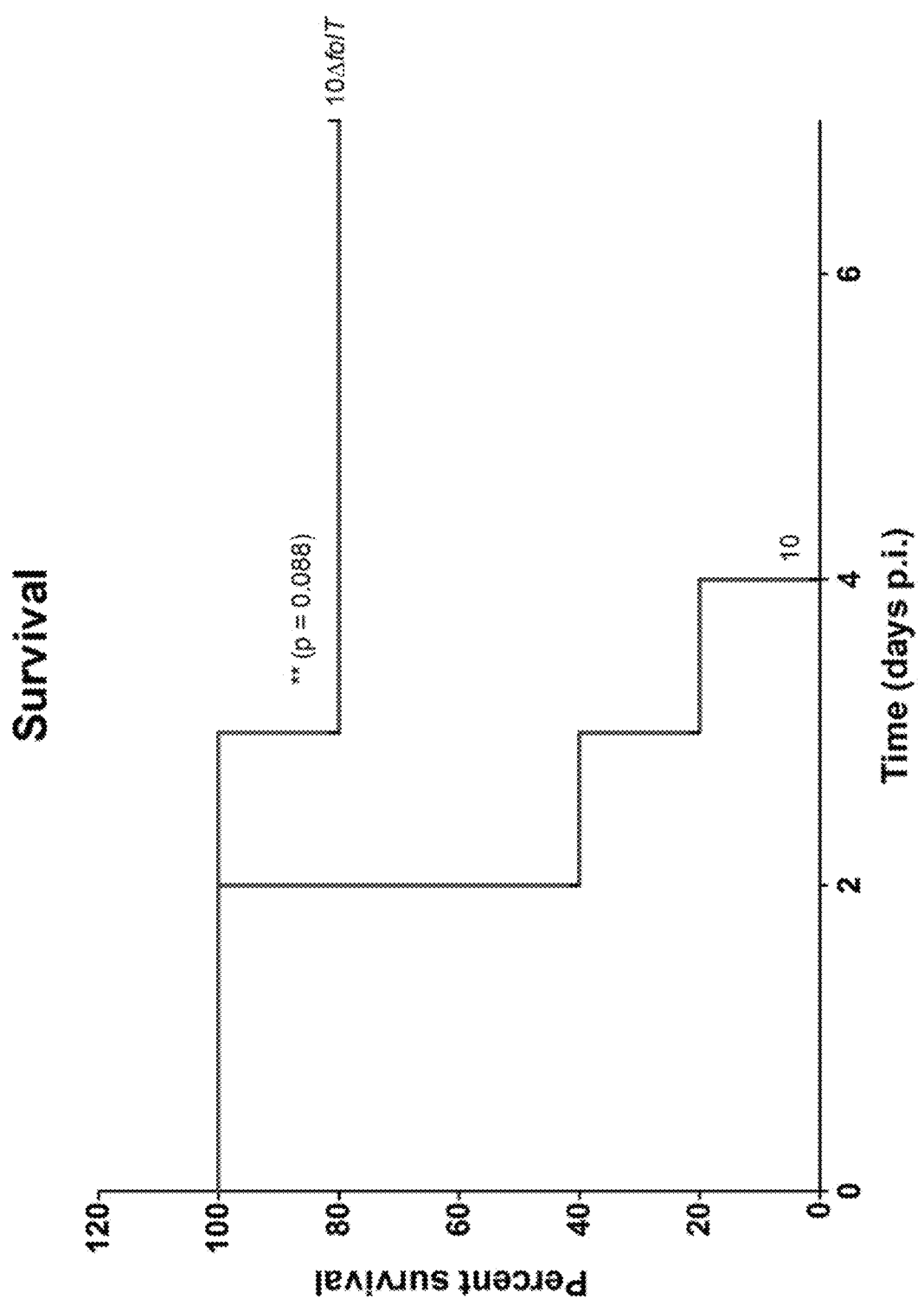

FIG. 10. Survival curves of pigs infected with *S. suis*, experiment 1. Pigs were infected either wild type strain 10 or with strain 10ΔfolT (CBS 140425). Pigs were euthanized when they reached predetermined humane end points for ethical reasons. Statistical analysis was done using Log-rank (Mantel-Cox) test.

Figure 11:
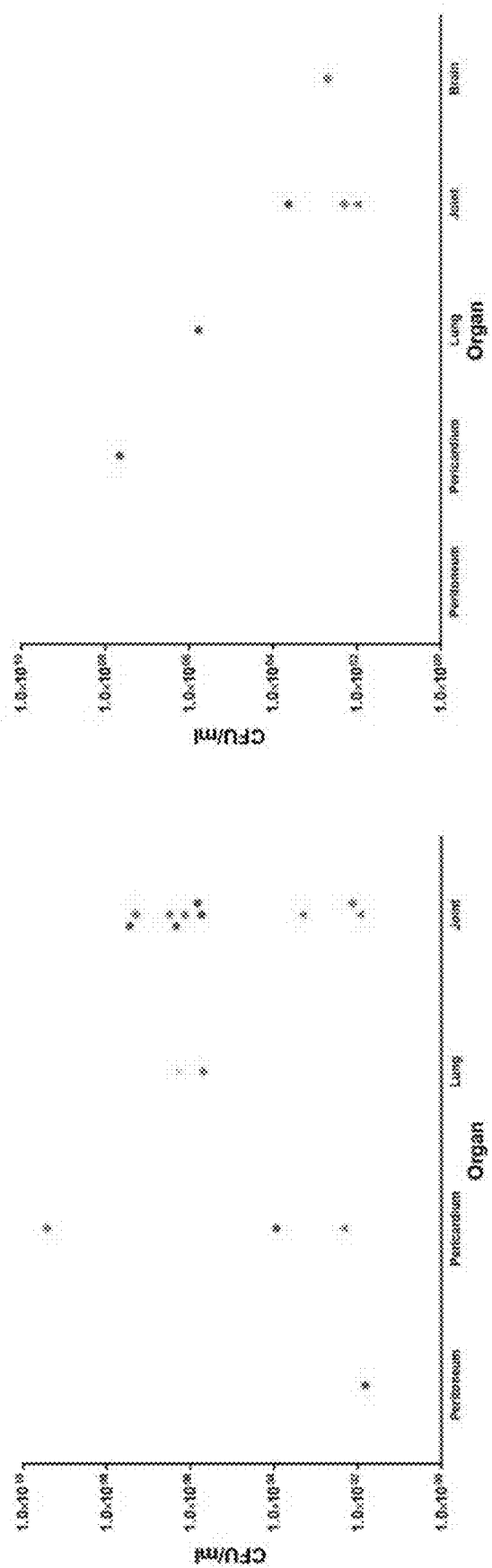

FIG. 11. Bacteriological examination of piglets infected with *S. suis*, experiment 1. Pigs were infected either wild type strain 10 or with strain 10ΔfolT (CBS 140425) Bacteria were enumerated by serial dilution and plating. Bacterial counts were calculated as CFU/ml. Different colours indicated different individual piglets.

Figure 12:
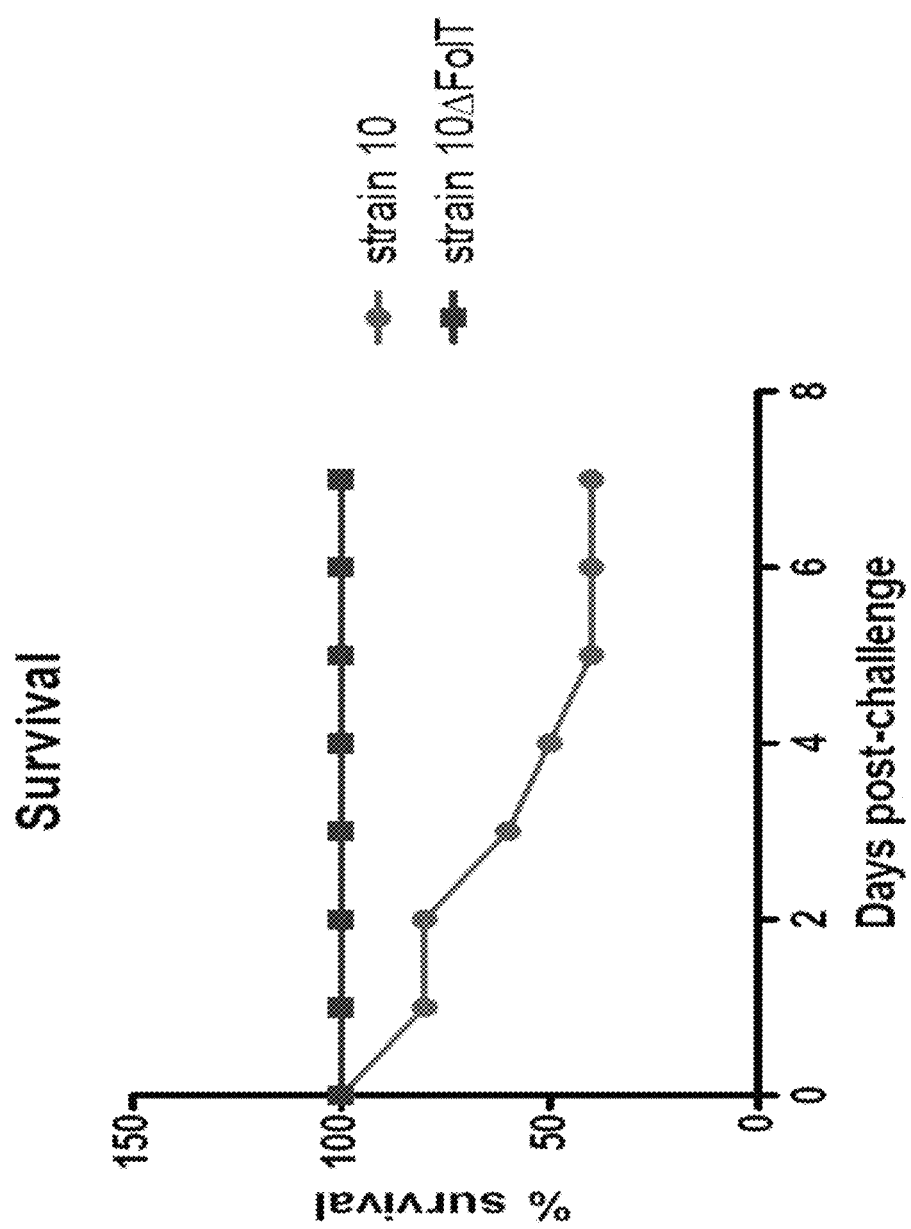

FIG. 12. Survival curves of piglets infected with *S. suis*, experiment 2. Piglets (n=10) were infected either with wild type strain 10 or with strain 10ΔfolT (CBS 140425) Pigs were euthanized when they reached predetermined humane end points for ethical reasons.

Figure 13:
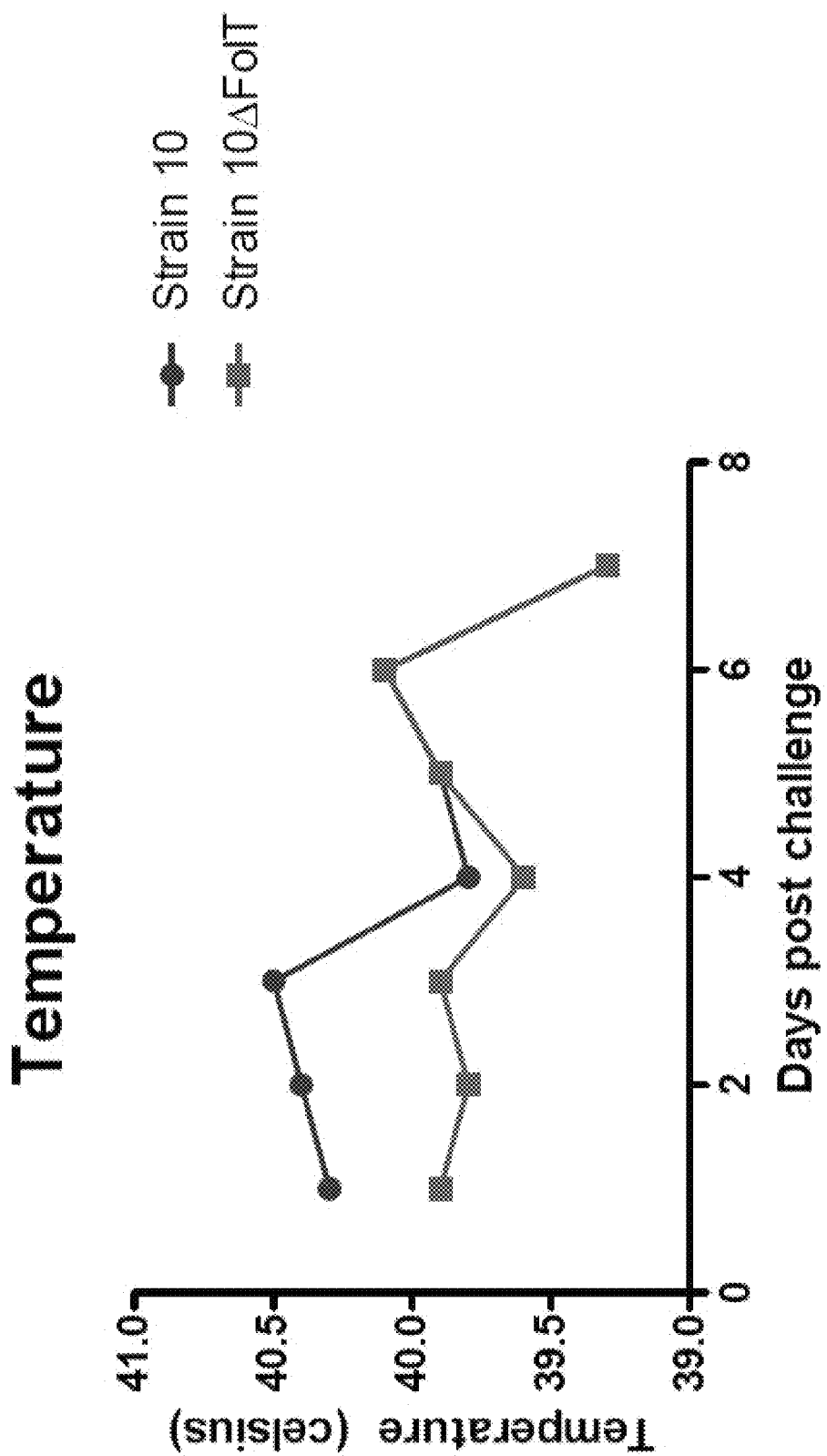

FIG. 13. Body temperature of piglets after *S. suis* infection, experiment 2. Averaged body temperatures of piglets (n=10) either infected with wild type strain 10 (blue) or with strain 10ΔfolT (CBS 140425) (green) are depicted.

Figure 14:
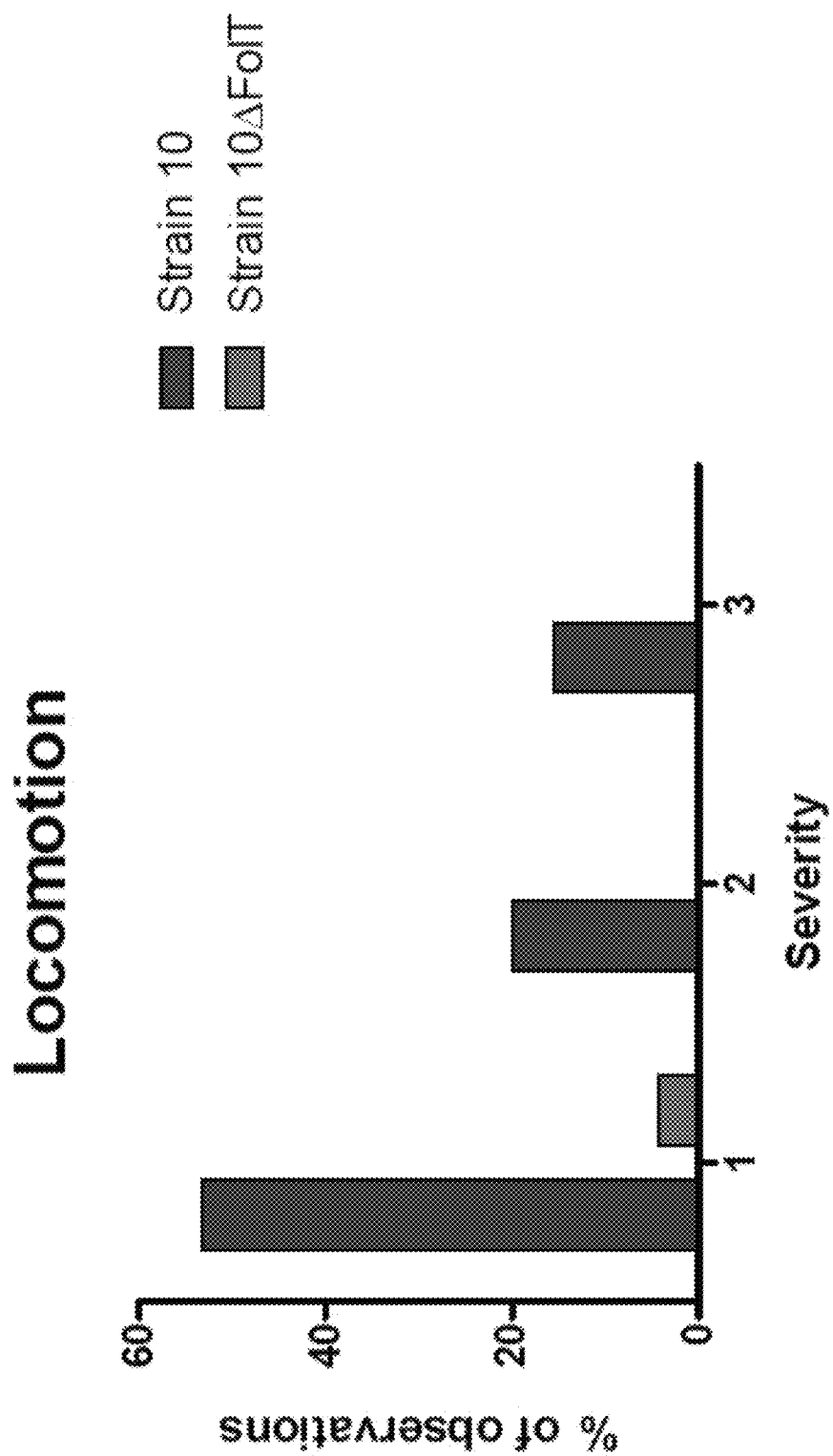

FIG. 14. Locomotion of piglets after *S. suis* infection, experiment 2. The percentage of positive observations in piglets either infected with wild type strain 10 (blue) or with strain 10ΔfolT (CBS 140425) are shown. Severity locomotion 1: mild lameness; 2: moderately lameness or reluctance to stand; 3: severe lameness (serving as a human endpoint)

Figure 15:
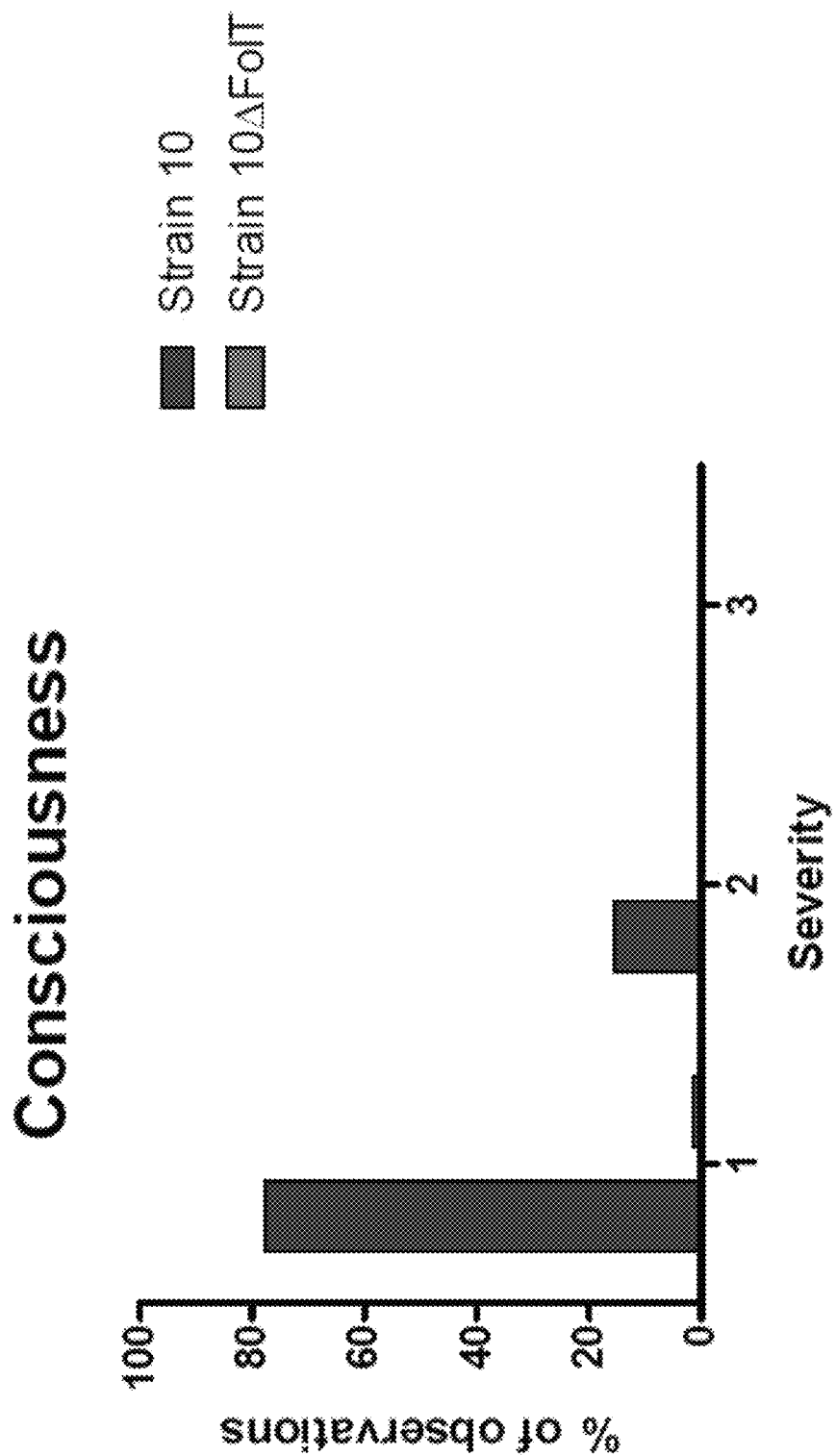

FIG. 15. Consciousness of piglets after *S. suis* infection, experiment 2. The percentage of positive observations in piglets either infected with wild type strain 10 (blue) or with strain 10ΔfolT (CBS 140425). Severity Consciousness: 1: depression; 2: apathy; 3: coma FIG. 16. Vaccination of pigs with the ΔFolT2 strain (CBS 143192) and protection after challenge with *S. suis* type 2. Pigs were vaccinated at day 1 and 21 with ΔFolT2 strain (CBS 143192). On day 35, the animals were challenged intraperitoneally (ip) with approximately $2\times10^9$ CFU of a virulent *S. suis* type 2 isolate. For seven days following challenge, the animals were observed for signs of disease associated with *S. suis*. Animals found dead or that had to be euthanized prior to off-test for animal welfare reasons were necropsied. The figure shows the percentage of animals that died or were euthanized following challenge (mortality).

FIG. 17. Vaccination of pigs with the ΔFolT strain (C513140425) and protection after challenge with *S. suis* type 2.

Pigs were vaccinated at day 1 and 21 with the ΔFolT strain (CBS 140425). On day 36, the animals were challenged intraperitoneally with approximately $2\times10^9$ CFU of a virulent *S. suis* type 2 isolate. Following challenge, the animals were observed for signs of disease associated with *S. suis* for seven days. Animals found dead or that had to be euthanized prior to off-test for animal welfare reasons were necropsied. The figure shows the percentage of animals that died or were euthanized following challenge (mortality).

DETAILED DESCRIPTION

Introduction

Previously, we used a complementation strategy to identify novel virulence factors, which might serve as vaccine candidates. Using this strategy, a hypervirulent *S. suis* isolate (S735-pCOM1-V[10]) was generated that causes severe toxic shock-like syndrome in piglets after infection resulting in death within 24 h post-infection[14]. S735-pCOM1-V[10] was selected from a library of clones generated in a weakly virulent serotype 2 isolate (S735), after transformation with plasmid DNA isolated from around 30,000 pooled clones carrying randomly cloned genomic DNA fragments from a virulent serotype 2 isolate (strain 10). Isolates with increased virulence were selected by infecting piglets with strain S735 containing the plasmid library of genomic fragments from strain 10. One prevalent clone isolated from the infected piglets contained a 3 kb genomic fragment from strain 10 designated V[10] and was demonstrated to be hypervirulent in subsequent animal experiments. V[10] contained an incomplete open reading frame (ORF), followed by two genes (orf2 and folC) in an operon structure as well as a second incomplete ORF. Assuming that only the full-length ORFs could contribute to the hypervirulence of this isolate, we further characterized the orf2-folC-operon. The first ORF in the operon could not be annotated and was designated orf2, the second ORF in the operon showed homology to the gene encoding polyfolylpolyglutamate synthase (FolC). This operon was present in all *S. suis* serotypes, including the parent strain S735. Strain S735 with low virulence, contained several single nucleotide polymorphisms (SNP) in orf2-folC and the non-coding regions compared to strain 10. Both genes of the operon that increased the virulence may be putative virulence factors and, if so, could be putative vaccine candidates. Here we investigated 1) whether the hypervirulence of the orf2-folC-operon is caused by orf2 or by folC or both and 2) the effect of a single nucleotide polymorfism in the promotor region of the orf2-folC-operon on virulence.

Materials and Methods

Bacterial Strains and Plasmids

*S. suis* isolates were grown in Todd-Hewitt broth (Oxoid, London, United Kingdom) and plated on Columbia blood base agar plates (Oxoid) containing 6% (vol/vol) horse blood. *Escherichia coli* was grown in Luria Broth and plated on Luria Broth containing 1.5% (wt/vol) agar. If required, erythomycin was added at 1 µg ml$^{-1}$ for *S. suis* and at 200 µg ml$^{-1}$ for *E. coli*. *S. suis* strain S735 complemented with a plasmid containing a 3 kb genomic fragment derived from strain 10 (S735-pCOM1-V[10]) and the other *S. suis* strains used in this study have been previously described (FIG. 1).

Example 1 Complementation of *S. suis* Strain S735

S735 was complemented with plasmid pCOM1 containing one of the two ORFs in the V[10] operon (i.e. orf2[10], or folC[10]) preceded by the putative promoter region of the operon from strain 10 or with plasmid pCOM1 containing orf2 and the cognate upstream promoter from strain S735 (orf2[S735]) (FIG. 1). To construct these plasmids, primers with restriction sites were designed to amplify orf2[10] or orf2[S735] (connE1-connE2), folC[10] (comE4-comE6) or the promoter region of the operon (connE1-comE3) (Table 1). The resulting PCR products orf2[10] and orf2[S735] were digested using restriction enzymes SacI and BamHI, cloned into pKUN19 [15], digested with the same restriction enzymes and subsequently cloned into pCOM1, yielding pCOM1-orf2[10] and pCOM1-orf2[S735], respectively. The PCR amplicon of folC[10] was digested using restriction enzymes SmaI and BamHI and cloned into pKUN19 cleaved with the same restriction enzymes. The PCR product comprising the promoter region of V[10] was cloned in front of folC[10] using restriction enzymes SacI and SmaI. Subsequently, the complete fragment of promoter V[10]-folC[10] was digested from pKUN19 using SacI and BamHI and cloned into pCOM1 digested with the same restriction enzymes, yielding pCOM1-folC[10]. To confirm that the fusion product of promoter—folC[10] was transcribed, in vitro transcription/translation was performed using $^{35}$S-methionine. A clear band of the molecular weight of FolC (46.8 kDa) was detected demonstrating that the fusion product could be expressed and translated (FIG. 2). All plasmids were introduced into *S. suis* strain S735 by electroporation. In addition, pCOM1-V[10] was introduced into the avirulent serotype 2 strain T15 by electroporation to yield T15-pCOM1-V[10].

Example 2 Experimental Infection with Complemented Isolates

Experimental infection of caesarean derived germ-free piglets was performed as previously described [14]. Prior to infection, germ-free status of piglets was confirmed by plating tonsil swabs on Columbia agar plates containing 6% horse blood. Briefly, 4 or 5 one-week-old germ-free pigs were infected intravenously with $10^6$ colony-forming units (CFU) of *S. suis* and then immediately orally administered 40 mg $kg^{-1}$ body weight of erythomycin (erythomycin-stearate, Abbott B. V., Amstelveen, The Netherlands) twice a day to keep selective pressure on *S. suis* isolates harbouring the pCOM plasmids. Infected pigs were monitored twice daily for clinical signs and tonsil swabs collected for bacteriological analysis. Pigs were euthanized when clinical signs of arthritis, meningitis, or sepsis were observed after infection with *S. suis*. Tissue specimens of CNS, serosae and joints were collected during necropsy, homogenized and bacterial cell counts were determined by plating serial dilutions on Columbia agar plates containing 6% horse blood and 1 μg $ml^{-1}$ of erythomycin. To be able to compare results from different animal experiments included herein, a uniform scoring of non-specific and specific symptoms was applied to all animal experiments. Non-specific symptoms included inappetite and depression that were scored 0 (none), 0.5 (mild inappetite/depression) or 1 (severe inappetite/depression). Specific symptoms included lameness, central nervous system (CNS) symptoms (locomotive disorders like cycling, or walking in circles; opistotonus; nystagmus), as well as raised hairs, arched back (kyphosis), and shivering, since these are all symptoms of sepsis or serositis. Based on these observation clinical indices were calculated by dividing the number of observations where either specific or non-specific symptoms were observed by the total number of observations for this parameter. This represents a percentage of observations where either specific or non-specific symptoms were observed. A similar approach was taken for the 'Fever Index'. Fever was defined as a body temperature >40° C. 'Mean number of days till death' was used as a survival parameter. Although animals were euthanized after reaching humane end points (HEP), the time between inoculation and reaching HEPs is still indicative of severity of infection. It is calculated by averaging the survival in days from inoculation until death.

Animal experiments with strain CBS 140425 were performed at the premises of Central Veterinary Institute of Wageningen UR, Lelystad, The Netherlands (now named Wageningen Bioveterinary Research (WBVR)) and were approved by the ethical committee of the Central Veterinary Institute of Wageningen UR, Lelystad, The Netherlands, in accordance with the Dutch law on animal experiments (#809.47126.04/00/01 & #870.47126.04/01/01). Animal experiments with strains CBS 140425 and 143192 were also performed in accordance with the US law on animal experiments.

Statistical analyses were performed on clinical indices of the groups (fever index, specific symptoms and non-specific symptoms) using a non-parametric Kruskal-Wallis test, as there was no homogeneity of variance among groups. In subsequent analyses, all groups were compared pairwise to the control group (S735-pCOM1) on all three parameters, using Mann-Whitney U tests. Differences were considered statistically significant at $p<0.05$. Calculations were performed using SPSS 19 (IBM, New York, USA).

Example 3 Experimental Infection with Strain 10ΔfolT (CBS 140425), Experiment 1

Ten 4-week-old piglets were housed at CVI animal facility in two groups of five animals. Piglets had ad lib access to feed and fresh water. A light provided animals with warmth and play material was available throughout the experiment. Prior to the start of the experiment, tonsil swabs of piglets were screened by PCR on colonization of S. suis serotype 2. Only PCR-negative piglets were included in the experiment. After ten days, animals were infected intravenously with either $1.1 \cdot 10^6$ CFU of wild type strain 10 or with $9.2 \cdot 10^5$ CFU mutant strain 10ΔfolT in the vena jugularis. Prior to infection basal temperatures of piglets were monitored daily for a period of three days. EDTA blood was collected prior to infection to obtain pre-infection plasma samples, as well as basal levels of white blood cell (WBC) numbers. Infected pigs were monitored three times a day at 8 pm, 3 am and 9 am for clinical signs. Non-specific symptoms included lack of appetite and depression, whereas, specific symptoms included lameness, central nervous system (CNS) symptoms (locomotive disorders like cycling, or walking in circles; opistotonus; nystagmus), as well as raised hairs, arched back (kyphosis), and shivering, all of which are symptoms of sepsis or serositis. Tonsil and faecal swabs were collected daily for bacteriological analysis. Blood was collected daily for bacteriological analysis, WBC counting and plasma collection. Pigs were euthanized when clinical signs of arthritis, meningitis, or sepsis were observed after infection with S. suis. At necropsy, internal organs (kidney, liver, spleen, peritoneum and pericardium) were bacteriologically screened for S. suis by plating on Columbia agar plates containing 6% horse blood. Organs that were macroscopically affected by S. suis, like purulent arthritis joints, pericarditis or peritonitis were plated in serial dilution to determine the bacterial load. Tissue specimens of these organs were fixated in formalin for histological examination. The animal experiment was approved by the ethical committee of the Central Veterinary Institute of Wageningen UR, Lelystad, The Netherlands, in accordance with the Dutch law on animal experiments (#2014011).

Example 4 Experimental Infection with Strain 10ΔfolT (CBS 140425), Experiment 2

In a second experiment, approximately 3-week old piglets (Commercial Cross) were used. The piglets had not been vaccinated against S. suis, had been obtained from a PRRSV negative herd, had never received medicated feed and were tonsil swab negative for S. suis serotype 2 by PCR upon enrolment. Treatment groups (10 piglets each) were housed separately. Animals were inoculated intravenously with either 3.48E+07 CFU of wild type strain 10 or with 1.45E+07 of mutant strain 10ΔfolT. The animals were observed once a day for clinical signs of S. suis associated disease (e.g. increase in body temperature, lameness, and changes in behaviour) for 7 days. Any animals displaying clinical signs that reached humane end-points (e.g. CNS signs, debilitating lameness) were euthanized to minimize suffering. Euthanized animals were necropsied to identify lesions typically associated with S. suis disease. Animals surviving to the end of the observation period were likewise euthanized and necropsied.

Example 5a Vaccination of Pigs with ΔFolT2 Strain (CBS 143192) and Protection after Challenge with S. suis Type 2

The study was conducted in commercial cross pigs; on the day of first vaccination, the pigs were 21±7 days of age. The animals had not been vaccinated against S. suis, were tonsil swab negative for S. suis type 2 by PCR, PRRSV negative by serology and originated from sows that were tonsil swab negative for S. suis type 2 by PCR. The study groups, the vaccination route and dose, the days of vaccination, and the day and route of challenge are listed in Table 6. The media used are described in Table 7.

On day 34, blood and tonsil swabs were collected from all animals, and then the strict control animals were moved to a separate airspace while all other groups were commingled. On day 35, the animals were challenged intraperitoneally (i p) with approximately $2 \times 10^9$ CFU of a virulent S. suis type 2 isolate.

For seven days following challenge, the animals were observed for signs of disease associated with S. suis. Animals found dead or that had to be euthanized prior to off-test for animal welfare reasons were necropsied. During necropsy, the animals were assessed for macroscopic signs typically associated with S. suis disease and a CNS (i.e. brain) and joint swab were collected. At off-test, all remaining animals were euthanized, necropsied and samples collected.

The preparation of the vaccines and placebo are listed in Table 7.

The preparation of the challenge material is listed in Table 8.

Figure 16:
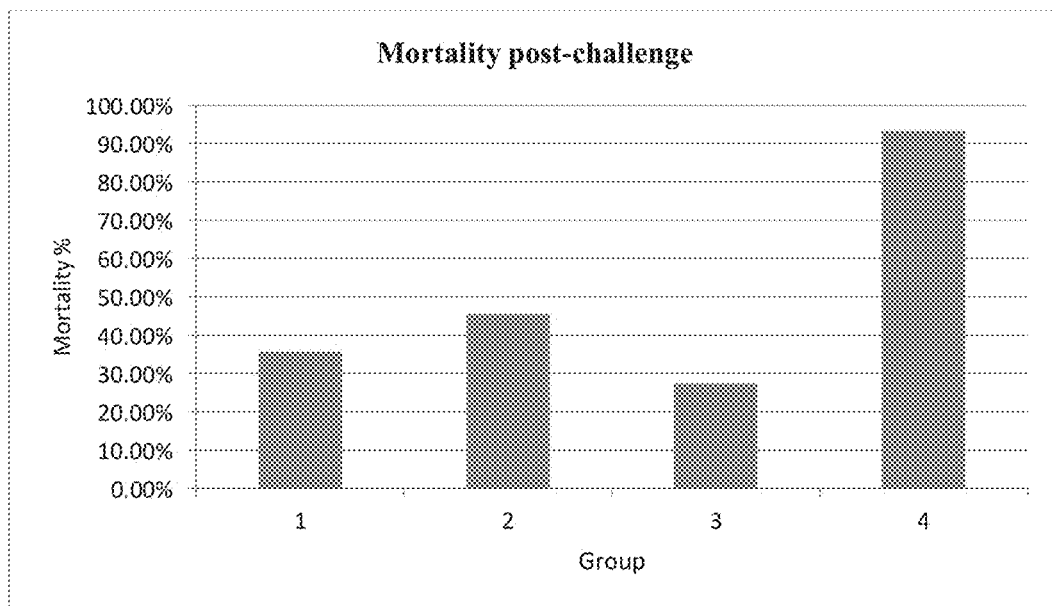

Vaccination with the S. suis ΔFolT mutant reduced the number of animals that died or had to be euthanized for animal welfare reasons during the post-challenge observation period (see Table 9 and FIG. 16). In addition, vaccination with the ΔFolT reduced findings of severe lameness (ie. the number of animals being unable to stand or being reluctant to stand), as well as findings of apathy in which the animals showed very limited to no interest in the environment (see Tables 10 and 11).

During necropsy, signs of inflammation in the brain, indicated by the presence of fibrin and/or fluid, were less frequently observed in ΔFolT vaccinated animals compared to the negative controls (see Table 12).

The S. suis challenge isolate was less frequently recovered from the brain and the joint swabs collected at necropsy from animals vaccinated with the ΔFolT strain compared to the negative controls (see Tables 13 and 14).

Example 5b Vaccination of Pigs with Strain 10ΔfolT (CBS 140425) and Protection after Challenge with S. suis Type 2

The study was conducted in commercial cross pigs, 21+/−5 days at the day of the first vaccination. The animals had not been vaccinated against S. suis, were tonsil swab negative for S. suis type 2 by PCR, PRRSV negative by serology and originated from sows that were tonsil swab negative for S. suis type 2 by PCR. The study groups, the number of animals/group at the time of study initiation, the vaccination dose, the days of vaccination, the vaccination route, the day of challenge and the challenge route are listed in Table 15.

On day 35, blood and tonsil swabs were collected from all animals and the strict control animals were euthanized. On day 36, the animals were challenged intraperitoneally with approximately $2 \times 10^9$ CFU of a virulent S. suis type 2 isolate.

Following challenge, the animals were observed for signs of disease associated with S. suis for seven days. Animals found dead or that had to be euthanized prior to off-test for animal welfare reasons were necropsied. During necropsy, the animals were assessed for macroscopic signs typically associated with *S. suis* disease and CNS swabs were collected. At off-test, all remaining animals were euthanized, necropsied and samples collected.

The preparation of the vaccine and placebo is listed in Table 16. The preparation of the challenge material is listed in Table 17.

The *S. suis* Farr mutant reduced the number of animals showing lameness following challenge, the number of animals showing abnormal behavior (i.e. depression, coma) following challenge as well as the number of animals that died or had to be euthanized for animal welfare reasons during the post-challenge observation period (see Table 18, 19 and 20 and FIG. 17).

At off-test (i.e. at day 7 following challenge or upon removal from the study due to death or euthansia) the animals were observed for abnormal findings in the brain (i.e. fibrin, fluid) as well as in the thoracic cavity (i.e. fibrin, fluid, lung congestion, pneumonia). In addition, samples were collected from the brain for the recovery of *S. suis*. The results are listed in Table 21, 22 and 23.

Example 6 cDNA Synthesis and Quantitative PCR

RT-PCR

Two hundred ng of RNA was used to synthesize cDNA in a reaction containing 25 ng $\mu l^{-1}$ random primers (Promega, Madison, WI, USA), 10 mM dNTPs (Promega), 10 mM DTT (Invitrogen), 40 U RNAsin (Promega) and SuperScript II Reverse Transcriptase (Invitrogen) according to manufacturer's instructions.

qPCR cDNA was diluted 20 times for qPCR analysis. Primers were designed using PrimerExpress software (Applied Biosystems, Foster City, CA, USA) (Table 1). Each reaction contained 12.5 pmol forward primer, 12.5 pmol reverse primer and POWR SYBR Green PCR Master Mix (Applied Biosystems) according to manufacturer's instructions. qPCR was performed using an AB17500 (Applied Biosystems). GeNorm software (GeNorm) was used to determine the most stably expressed reference genes. For *S. suis* recA was the least variable in expression of the 6 potential reference genes (phosphogelycerate dehydrogenase (pgd), acetyl-coA acetyltransferase (aca), mutS, glutamate dehydrogenase (gdh) tested. Genorm combines expression data into a number representing stability of expression, where 1 represents the most stabile gene. Stability numbers for *S. suis* ranged from 1.667 for gdh to 1.217 for recA. The level of expression of these reference genes was measured to control for variation in RNA-yield and RT-reaction conditions. In each qPCR run a standard curve was incorporated consisting of a vector containing a cloned PCR product of the target gene of that reaction. The standard curve consisted of seven 10-fold dilutions of the control vector. In this way both the expression level of the target gene and the expression levels of external reference genes could be calculated from a standard curve. For each reaction water was included in place of cDNA or template as a negative control. Analysis was performed using the AB17500 Software (Applied Biosystems).

Sequence Analysis

Sequence reactions and analysis were performed by Baseclear (Leiden, The Netherlands).

Example 7 Site-Directed Mutagenesis

Site directed mutagenesis was achieved using the Quickchange II site-directed mutagenesis kit (Agilent Technologies, La Jolla, CA, USA) according to manufacturer's instructions. PCR primers were designed with the accompanying software (Agilent Technologies) (Table 1). Using primers t448a and t488a_antisense the plasmid pCOM-orf2 [5735] was amplified, introducing the desired mutation that changed the −35 region of the putative promotor region of the orf2-folC-operon of S735 from 5'-TGGTCA-3' to 5'-TGGACA-3' (FIG. 1). The reaction mixture was digested using DpnI to inactivate the original template vector and subsequently transformed to XL-1-blue competent cells (Invitrogen). To exclude the possibility of introducing PCR errors into the vector backbone, the insert of the plasmid (orf2[S735]) was isolated from the template vector after digestion with restriction enzymes BamHI and SacI and cloned into pCOM1 digested with the same restriction enzymes. The resulting plasmid was introduced into *S. suis* isolate S735 by electroporation and transformants were selected on Columbia agar containing 1 µg ml$^{-1}$ erythomycin, yielding S735-pCOM1-orf2[S735][t488a]. Sequencing was used to exclude presence of PCR errors in the final construct.

Example 8 Construction Knock-Out Mutant of *S. suis* Folate Substrate Binding Protein (folT)

An isogenic folT knock out mutant was constructed in strain 10 by disrupting folT with a Spectinomycin resistance cassette. pCOM1-V[10] was digested with BamHI and ligated into BamHI digested pKUN plasmid, yielding pKUN-V[10]. To remove 3' part of V[10], pKUN-V[10] was digested with SphI after which the vector fragment was purified and ligated, yielding pKUN-V[10]*. pKUN-V[10]* was partially digested with XmnI, the linear vector fragment was purified and ligated with the blunt end Spectinomycin resistance cassette, yielding pKUN-V[10]*-Spec$^R$. For construction of the mutant V[10]*-Spec$^R$ was amplified by PCR using V735-fw and M13-rev. The PCR product was purified using the PCR Purification Kit (Qiagen). The purified PCR-product was used transform *S. suis* strain 10 using ComS as competence inducer as described by Zaccaria et al. to induce homologous recombination. Transformants were selected on Columbia agar plates containing 6% (vol/vol) horse blood and 100 µg ml$^{-1}$ spectinomcyin. Double crossovers were checked by PCR and confirmed using Southern blotting. To exclude the possibility of introduction of point mutations, chromosomal DNA of the isogenic knockout mutant was isolated and transformed to strain 10. Again mutants were selected on Columbia agar plates containing 6% (vol/vol) horse blood and 100 µg ml$^{-1}$ spectinomcyin, and screened by PCR, yielding strain 10ΔfolT. This prototype recombinant ΔFolT mutant strain has been deposited as "CBS 140425 *Streptococcus suis* ΔFolT mutant" at the Centraalbureau voor Schimmelcultures for the purpose of patent procedure under the Regulations of the Budapest Treaty at Aug. 19, 2015.

Example 9 ΔfolT Deletion Mutants not Containing the Spectinomycin Resistance Gene A ΔfolT deletion mutant not containing the Spectinomycin resistance gene was constructed as well. For this the thermosensitive shuttle vector pSET5s (Takamatsu, D., Osaki, M. and Sekizaki, T. 2001. Plasmids 46: 140-148) was used. Plasmid pSET5s contains a temperature sensitive origin of replication and can be propagated at 37° C. in *E. coli*, but replication of the plasmid is blocked above 37° C. in *S. suis* (Takamatsu et al). pSET5s contains a cloramphenicol resistance gene (Cm) that can be used for selection of transformants in *E. coli* as well as in *S. suis*. A prototype recombinant ΔFolT mutant strain not containing the Spectinomycin resistance gene has been deposited as "CBS 143192 *Streptococcus suis* ΔFolT2 mutant" at the Westerdijk Fungal Biodiversity Institute for the purpose of patent procedure under the Regulations of the Budapest Treaty at Aug. 25, 2017.

To construct a ΔfolT mutant isolate, a PCR product containing the 5'- and 3'-flanking sequences of the folT gene was generated. This fragment is cloned into pSET5s and Cm resistant transformants are selected at 37° C. in *E. coli*. The plasmid was then isolated from *E. coli* and introduced into *S. suis* strain 10. Transformants were selected on Columbia agar plates at 30° C. containing Cm. A transformed colony was used to inoculate 1 ml of Todd Hewitt Broth (THB) containing Cm and the culture was grown overnight at 30° C. The overnight culture was diluted 100-fold in the same medium and was incubated as above until an optical density at 600 nm of 0.2-0.3 is reached, at which the culture is transferred to 38° C. At this temperature, the plasmid is unable to replicate. This step selects for strains in which the plasmid has integrated into the chromosome via a single recombination event. Serial dilutions of this culture were plated at Columbia horse blood plates containing Cm. Plates were incubated overnight at 38° C. A colony containing the recombinant plasmid integrated into the chromosome was picked and inoculated into 1 ml of Todd Hewitt Broth (THB) with Cm for incubation overnight at 38° C. The culture was diluted 100-fold with Cm-free THB and grown at 28° C. for five subsequent passages. At this temperature, the plasmid is able to replicate and is excised from the chromosome via a second recombination event over the duplicated target gene sequence. The excision of the plasmid can yield the wild type genotype or can result in a folT deletion mutant. Serial dilutions of the culture were plated onto Columbia horse blood plates (without Cm) and incubated overnight at 38° C. Single colonies were then replica plated onto Columbia horse blood plates with and without Cm. Cm sensitive colonies were screened by PCR to identify the ΔfolT mutant isolates not containing the Spectinomycin resistance gene.

Hybridization Studies

Chromosomal DNA was isolated from stationary growing *S. suis* cultures. Two hundred nanogram of purified DNA was spotted onto Genescreen-Plus (Perkin Elmer, USA). Labelling of probes with 32 P, hybridization and washing was done as described before [17]. PCR products of folT and folC were used as a probe, whereas a 16S rRNA probe was used as positive control.

Overexpression of folT Suffices to Induce Hypervirulence in Strain S735

Introduction of a 3 kb genomic fragment from virulent serotype 2 strain 10, V[10], increased the virulence of the weakly virulent serotype 2 strain S735 [14], creating a hypervirulent isolate (S735-pCOM1-V[10]). All pigs infected with S735-pCOM1-V[10] died within 1 day post infection (p.i.) and a high percentage of the pigs showed severe clinical signs of disease (Table 2), whereas nearly all pigs infected with the control strain S735-pCOM1 survived throughout the experiment. Clinical indices differed significantly (p 0.01) between pigs infected with S735-pCOM1-V[10] and S735-pCOM1 (Table 2). As a control, we also tested the virulence of S735 transformed with a plasmid containing the homologous 3 kb fragment from strain S735 (S735-pCOM1-V[S735]). A high percentage of the pigs infected with S735-pCOM1-V[S735] survived throughout the experiment. In contrast pigs infected with S735-pCOM1-V[S735] showed significantly more specific clinical signs (p 0.01) than pigs infected with S735-pCOM1 (Table 2), although differences in clinical indices for fever and non-specific symptoms were not significantly different between the groups (p=0.06). Thus, the increased copy number of V[S735] in S735, due to introduction of plasmid pCOM1-V[S735] increased specific clinical signs of *S. suis*. Nevertheless, the specific and non-specific clinical signs due to porcine infection with S735-pCOM1-V[10] (p 0.01) were significantly increased compared to pigs infected with S735-pCOM1-V[S735], demonstrating that the introduction of V[10] in strain S735 increased the virulence more than introduction of V[S735]. This result indicated that hypervirulence of strain S735 pCOM-1-V[10] might be due to the different nucleotide polymorphisms in V[10] compared to V[S735].

To determine if the both the orf2 and the folC-genes are required for the observed increase in virulence, both genes of the operon obtained from strain 10 preceded by its cognate promoter sequence were introduced separately into strain S735 to generate strains S735-pCOM1-orf2[10] and S735-pCOM1-folC[10]. Virulence of these isolates was determined in an experimental infection in piglets, using S735-pCOM1-V[10] and S735-pCOM1 as controls. Table 2 shows that pigs infected with S735-pCOM1-V[10] or with S735-pCOM1-orf2[10] died within one day p.i. with severe clinical signs. Infected pigs developed toxic shock-like syndrome that was not observed using wild-type strain 10 in experimental infections, implying fragment V[10] and orf2 [10] increased virulence of S735 yielding more virulent isolates than strain 10 [3]. Both specific and non-specific symptoms were significantly increased ($p<0.01$) in pigs infected with S735-pCOM1-V[10] or with S735-pCOM1-orf2[10] compared to S735-pCOM1 (Table 2).

Bacteriological examination showed that CNS, serosae and joints were colonized by high CFU of *S. suis*. In contrast pigs infected with S735-pCOM1-folC[10] or S735-pCOM1 lived throughout the experiment (11 days p.i.) showing mild symptoms of infection, like fever. No significant differences in clinical outcome were observed between pigs infected with S735-pCOM1-folC[10] and with S735-pCOM1. This clearly demonstrates that introduction of folC[10] does not increase the virulence of strain S735, whereas introduction of V[10] and orf2[10] increased the virulence of strain S735. Therefore, we concluded that the observed increased virulence of S735-pCOM1-V[10] compared to S735-pCOM1 was attributed to introduction of orf2[10].

In conclusion, both copy number of V[10] and genetic background of the orf2-folC operon seem to be determinative in the virulence of a given isolate.

Datamining in Silico Data Demonstrates ORF2 is a Substrate Binding Protein Facilitating Folate Transport Now that the increased virulence was attributed to introduction of multiple copies of orf2[10], the putative function of orf2 was sought. In silico analysis of the 5' intergenic region preceding the orf2-folC operon revealed the presence of a predicted secondary structure, which showed strong homology to a tetrahydrofolate riboswitch (FIG. 3). Tetrahydrofolate riboswitches are a class of homologous RNAs in certain bacteria that bind tetrahydrofolate (THF) [18]. It is almost exclusively located in the probable 5' untranslated regions of protein-coding genes, and most of these genes are known to encode either folate transporters or enzymes involved in folate metabolism. For these reasons, it was inferred that the RNAs function as riboswitches. THF riboswitches are found in a variety of Firmicutes, specifically the orders Clostridiales and Lactobacillales, and more rarely in other lineages of bacteria. The THF riboswitch was one of many conserved RNA structures found in a project based on comparative genomics [19]. The relation with folate metabolism was confirmed by Eudes et al, demonstrating that in *S. suis* the gene upstream of folC encoded a folate transporter, Farr [20]. This annotation was also applied to the new genome sequence of *S. suis*, SC070731, where the homologous gene of ssu0135 was annotated to encode for Far (GenBank AGG63648.1). A 3-dimensional structure for the folate energy-coupling factor transport of *Lactobacillus brevis* was determined [21], leading to the proposal of a multi protein model of the folate transporter. In this model ORF2/FolT functions as the transmembrane substrate-specific binding protein. Together with a more generic transmembrane protein and two nucleotide-binding proteins forming the energy-coupling module this complex facilitates transmembrane transport of folate. Only the substrate-binding protein (Farr) is specific for folate, the other components are also used for transport of other substrates like thiamine or riboflavin. When the protein sequence of Far of *S. suis* was compared to putative Farr sequences of other organisms, it was clear that conserved amino acids were also conserved in *S. suis* (FIG. 4). Interestingly, FIG. 4 also shows that the arginine that was extremely conserved in the human folate transporter as well as in *Escherichia coli* tetracycline transporters was also conserved in *S. suis* (Arg99) folT suggesting this residue to be important for transporters ranging from men to bacteria [22]. Taken together, these data strongly suggest that the conserved protein of unknown function, ORF2, identified using a complementation strategy encodes a substrate binding protein facilitating folate transport.

Folate Transport in *Streptococcus suis*

Sequence analysis of P1/7 (that is highly homologous to the genome of strain 10) indicates that *S. suis* encodes all enzymes required to synthesize tetrahydrofolate (THF) via the classical folate biosynthesis pathway (FIG. 5). Based on data available in the KEGG database (www.kegg.ip) folate metabolism in *S. suis* makes use of the classical folate pathways using folE, folQ, folB, folK, folC, folA and substrates GTP, p-aminobenzoate (PABA) and glutamyl (GLU) as depicted in the scheme. However, with the additional genes present on the V[10] operon, *S. suis* seems also capable of inducing expression of foiI to directly import folate and using the simultaneous induced expression of the additional copy of folC, folate can immediately be processed to the endproduct tetrahydrofolate (THF). In this way the combination of folT and folC forms an additional 'shortcut' that allows production of THF. The presence of the THF riboswitch upstream of the folT-folC operon suggests tight regulation of this two-gene operon that might imply that the folT-folC operon is only expressed under specific conditions, e.g. folate poor conditions. Based on the results of the animal experiment described above, it is suggested that the folT-folC operon is at least expressed under in vivo conditions.

Presence and Expression of folT in *Streptococcus suis*

Presence of the folT gene was demonstrated in all *S. suis* serotypes tested with exception of serotypes 32, and 34. However, serotypes 32 and 34 were re-assigned to belong to the genus of *Streptococcus orisratti*, instead of *S. suis* [1]. So, in conclusion, all *S. suis* serotypes are deemed to have the genes encoding FoiI and FolC.

Sequence analysis of the putative promoter of orf2 revealed a difference at one nucleotide position in the −35 region of the putative promoter in strain 10 (TGGACA) compared to strain S735 (TGGTCA) [14]. The effect of this SNP on expression levels of orf2 and folC in strains 10 and S735 was determined using qPCR analysis. Significantly higher levels of expression of orf2 as well as folC were observed in strain 10 compared to strain S735 (FIG. 6A). This clearly indicates that the SNP in the −35 region of the putative promoter affects the transcription of orf2 and folC. Thereby, it demonstrates that the identified SNP was indeed located in the promoter region co-transcribing orf2 and folC in an operon. Moreover, introduction of pCOM1-orf2[10] into S735 increased expression of orf2 31-fold compared to introduction of pCOM1, whereas introduction of pCOM1-orf2[S735] increased expression of orf2 only 5-fold (FIG. 6B). As expected expression levels of folC were similar for both recombinant strains (FIG. 6B). To confirm that the identified SNP in the −35 region of the promoter is responsible for the differences in transcription of orf2 in strains S735 and 10 the TGGTCA of orf2[S735] was mutated to TGGACA as found in the promoter of orf2[10] (yielding strain S735-pCOM1-orf2[S735][t488a]. Transcript levels of orf2 in S735-pCOM1-orf2[S735][t488a] were shown to be similar to that of strain S735-pCOM1-orf2[10] and four-fold higher than that of strain S735-pCOM1-orf2[S735] in different growth phases (FIG. 6C). Both promoters are most active early in the growth phase of *S. suis* when grown in Todd Hewitt broth (FIG. 6C). Together, these results clearly demonstrate that in strain 10, the promoter upstream of orf2-folC-operon is stronger than the promoter upstream of this operon in strain S735, due to an SNP in the −35 region.

To determine whether the SNP linked to increased expression of orf2-folC operon was associated with particular clonal types or serotypes of *S. suis* the promoter regions of a large collection of isolates were sequenced (Table 3). All isolates used were recently characterized and typed by CGH and MLST [23]. Based on the sequence data obtained, isolates could be divided in two main groups (Table 3). The strong −35 promoter region was exclusively found in serotype 1 and 2 isolates that belonged to CGH cluster A and MLST clonal complex 1 and that expressed the EF-protein. The SNP associated with lower promoter activity was found in serotype 7 and 9 isolates belonging to CGH group B (except for two), which are all negative for the expression of EF, as well as in weakly virulent isolates of serotype 2 belonging to CGH group A/Clonal Complex 1 (CC1) that were positive for the expression of the larger form of EF protein (EF*). There were two exceptions; serotype 7 isolate (C126), that belongs to CC1 but does not express the EF-protein contained the SNP linked to a stronger promoter and serotype 7 isolate (7711) which had a different −35 promoter sequence (TTGTCA) for which the promoter strength is undetermined. In conclusion, only CC1 isolates expressing EF protein (and 1 serotype 7 isolate) contain the SNP linked to strong promoter activity. As isolates of this combination of phenotype and genotype are strongly correlated with virulence [23,24], we can conclude that a strong promoter upstream of orf2-folC-operon is associated with virulent isolates of *S. suis*. This observation, together with the increased virulence observed after introduction of additional copies of folT[10] suggests that increased expression of folT either due to increased copy number or due to a stronger promoter leads to increased virulence in *S. suis*.

Growth of *Streptococcus suis* with Additional Copies of folT or without folT in Culture.

No significant differences were observed in growth in culture of *Streptococcus suis* with additional copies of folT or without a functional folT in comparison to the parent strain in vitro.

Protein Expression of FolT

Based on the protein sequence of FoII it was predicted that FoiI is a very hydrophobic protein with at least 5 transmembrane domains. Homology modeling (Expacy server) using 6 known FoiI structures among which the published 3D structure of FoiI from *Lactobacillus brevis* a 3D structure for FoiI of *S. suis* was predicted (FIG. 7).

FolT is Important for Survival In Vivo: Virulence of a folT Knock-Out Strain 10ΔfolT Since overexpression of folT in a weakly virulent *S. suis* strain led to a strong increase of virulence, we hypothesized that FoiI plays an important role in vivo. To test whether this hypothesis is true, an isogenic knock-out was constructed in virulent *S. suis* strain 10 by inserting an spectinomycin-resistance cassette in the folT gene. Since folT and folC are in an operon structure, this knock-out will probably also be knocked out for the additional copy of folC. To determine whether folate transport is essential for virulence in vivo, in experiment 1, ten pigs were intravenously infected with either wild type strain 10 or knock out strain 10ΔfolT. All pigs responded to the inoculation with an increase of body temperature (FIG. 8). However, pigs infected with the wild type strain 10 showed higher temperatures for a longer period of time, compared to pigs infected with the knockout strain 10ΔfolT. This is also reflected by a difference in fever index (percentage of observations where pigs displayed fever) between both groups (p=0.06). This suggests that strain 10ΔfolT is less pyogenic, compared to the wild type strain. This might be a consequence of the fact that significantly fewer bacteria were isolated from the blood of piglets infected with strain 10ΔfolT. Only two pigs infected with strain 10ΔfolT showed a short bacteraemic period, compared to 5 pigs infected with strain 10; pigs infected with strain 10 also had significantly higher numbers of bacteria in their blood fora longer period of time (FIG. 9). This suggests, strain 10ΔfolT is either cleared more efficiently from the blood, or is unable to survive in blood. White blood cell counts revealed that pigs infected with wild types strain 10 showed a stronger increase of WBCs for a longer period of time. All pigs infected with strain 10 displayed increased WBCs, whereas only one of the pigs infected with strain 10ΔfolT showed increased WBCs. The calculated WBC index differs significantly between the groups (Table 5). Survival rates between the two groups differed significantly: pigs infected with strain 10 had an average survival of 2.6 days post infection, whereas pigs infected with strain 10ΔfolT survived 6.2 days p.i. (FIG. 10). Although pigs were euthanized when predetermined humane end points were reached, survival reflects the severity of infection. As is shown in FIG. 10, the survival curves differ significantly between the groups. Gross pathology revealed that 4/5 pigs infected with strain 10 showed clinical signs specific for a *S. suis* infection like arthritis, pleuritis, pericarditis or peritonitis, whereas 3/5 pigs infected with strain 10ΔfolT showed specific clinical signs. Bacteriological examination of all infected organs revealed that more organs were colonized by higher bacterial loads for the wild type strain 10 compared to strain 10ΔfolT (FIG. 11).

The second animal experiment (experiment 2) generally confirmed the data generated in experiment 1. As in the first experiment, the survival curves of wild type strain 10 and the strain 10ΔfolT isolate differed significantly. In experiment 2, all animals inoculated with strain 10ΔfolT survived until the end of the experiment, whereas 60% of the animals inoculated with strain 10 had to be euthanized in the course of the experiment (FIG. 12). Moreover, the frequency and severity of clinical signs (e.g. temperature, locomotion and consciousness; see FIGS. 13, 14, 15) differed considerably between animals inoculated with wild type strain 10 and strain 10ΔfolT. The frequency of gross pathological lesions in joints and peritoneum obtained at necropsy also differed considerably between the wild type and the 10ΔfolT mutant isolate.

Based on the results of the infection experiments in piglets, it was concluded that the isogenic knock out mutant strain 10ΔfolT was strongly attenuated compared to the wild-type strain. This shows that the folate transporter is required for bacterial survival under in vivo conditions. Taking the result from both studies together, these experiments clearly show that the ΔfolT isolate produced almost no mortality, minimal clinical signs, and a reduced frequency of joint inflammation and peritonitis compared to the parent strain. It can therefore be concluded that a ΔfolT strain is highly attenuated and safe.

Summary Results. A Vaccine Comprising a Bacterium Provided with a Modification Such as a Mutation, Deletion or Insertion in the DNA Region Encoding for the Folate Substrate Binding Protein (a ΔfolT Isolate) of Said Bacterium) of a Bacterium Protects Hosts Against Challenge with a Virulent Isolate of Said Bacterium not Having Said Modification.

The invention provides a method to produce a bacterium, preferably for use in a vaccine, preferably for use in a vaccine to generate protection against a bacterial infection, comprising selecting a parent bacterial strain generally capable of folate transport and folate synthesis and selecting a bacterium from that parent strain for having a modification such as a mutation, deletion or insertion in the DNA region encoding for the folate substrate binding protein (in *Streptococcus suis* known as the folT gene) of said bacterium and selecting said bacterium for the capacity to grow to similar rates as said parent strain in vitro but to grow to reduced rates compared with said parent strain in vivo. The invention also provides a method to produce a bacterium, preferably for use in a vaccine, preferably a vaccine for use to generate protection against a bacterial infection, comprising selecting a parent bacterial strain generally capable of folate transport and folate synthesis and transforming, preferably by recombinant means, a bacterium from that parent strain by providing it with a modification such as a mutation, deletion or insertion in the DNA region encoding for the folate substrate binding protein (in *Streptococcus suis* known as the folT gene) of said bacterium and selecting said bacterium for the capacity to grow to similar rates as said parent strain in vitro but to grow to reduced rates compared with said parent strain in vivo. Such a bacterium, as provided herein, still has the capacity to produce folate for its own use by applying its de novo folate synthesis pathways. Having these synthesis pathways intact leaves its capacity to in vitro growth (in culture) unaffected, surprisingly it was however shown herein that its growth and virulence in the host (in vivo) was strongly reduced.

Such a bacterial strain that grows well in vitro but in vivo grows less than its parent strain and has associated strongly reduced virulence in vivo is very useful as a vaccine strain. Such a strain or mutant as provided by the invention is, on the one hand, essentially unaffected in folate synthesis and thus able to be grown to high titres and thereby relatively easy and inexpensive to produce, while on the other hand it is, due to its reduced growth and reduced virulence in its host as compared to its parent strain, relatively innocuous after in vivo application, making it extremely useful as a vaccine directed against a bacterial infection.

In a first series of experiments herein, approximately three-week old piglets (Commercial Cross) that had not been vaccinated against *S. suis* and had never received medicated feed were used for the efficacy study. The animals were tonsil swab negative for *S. suis* serotype 2 by PCR upon enrolment and originated from a PRRSV negative herd. The two treatment groups were housed separately at the study site.

Upon arrival at the study site, blood and tonsil swabs were collected from all animals. On study day 0, following an appropriate acclimation period, one group of the animals were vaccinated with strain 10ΔFolT. Another group of animals was left unvaccinated. The vaccinated animals were revaccinated on day 21 into the right side of the neck with same dose of the mutant isolate, respectively. After each vaccination, the animals were observed for local and systemic reactions. On study day 35, blood and tonsil swabs were collected from all animals before the animals in both groups were challenged. with the challenge strain ATCC700794. The animals were observed for signs of *S. suis* associated disease (e.g. increase in body temperature, lameness, abnormal behaviour, CNS signs) for 7 days following the challenge. Animals found dead or that had to be euthanized prior to off-test for animal welfare reasons were necropsied. During necropsy, the animals were assessed for macroscopic signs typically associated with *S. suis* disease (e.g. inflammation of CNS, joints, thoracic cavity). In addition, a CNS swab was collected for recovery of the challenge isolate. On day 42, all remaining animals were euthanized, necropsied and sampled as described above. Vaccinated animals showed considerably less signs of *S. suis* disease after challenge.

A second series of experiments was conducted in commercial cross pigs; on the day of first vaccination, the pigs were 21±7 days of age. The animals had not been vaccinated against *S. suis*, were tonsil swab negative for *S. suis* type 2 PRRSV negative by serology and originated from sows that were tonsil swab negative for *S. suis* type 2. Upon arrival at the study site, blood and tonsil swabs were collected from all animals. On study day 0, following an appropriate acclimation period, one group of the animals were vaccinated into the left side of the neck with strain ΔFolT2. Another group of animals was left unvaccinated. The vaccinated animals were revaccinated on day 21 into the right side of the neck with the same dose the mutant isolate, respectively. After each vaccination, the animals were observed for local and systemic reactions. On day 34, blood and tonsil swabs were collected from all animals, and then the strict control animals were moved to a separate airspace while all other groups were commingled. On day 35, the animals were challenged intraperitoneally (ip) with approximately a virulent *S. suis* type 2 isolate.

For seven days following challenge, the animals were observed for signs of disease associated with *S. suis*. Animals found dead or that had to be euthanized prior to off-test for animal welfare reasons were necropsied. During necropsy, the animals were assessed for macroscopic signs typically associated with *S. suis* disease and a CNS (i.e. brain) and joint swab were collected. At off-test, all remaining animals were euthanized, necropsied and samples collected. Vaccination with the ΔFolT2 mutant reduced the number of animals that died or had to be euthanized for animal welfare reasons during the post-challenge observation period. During necropsy, signs of inflammation in the brain, indicated by the presence of fibrin and/or fluid, were less frequently observed in ΔFolT2 vaccinated animals compared to the negative controls. The *S. suis* challenge isolate was less frequently recovered from the brain and the joint swabs collected at necropsy from animals vaccinated with the ΔFolT2 strain compared to the negative controls.

REFERENCES

1. Hill J E, Gottschalk M, Brousseau R, Harel J, Hemmingsen S M, et al. (2005) Biochemical analysis, cpn60 and 16S rDNA sequence data indicate that *Streptococcus suis* serotypes 32 and 34, isolated from pigs, are *Streptococcus orisratti*. Vet Microbiol 107: 63-69.
2. Wisselink H J, Smith H E, Stockhofe-Zurwieden N, Peperkamp K, Vecht U (2000) Distribution of capsular types and production of muramidase-released protein (MRP) and extracellular factor (EF) of *Streptococcus suis* strains isolated from diseased pigs in seven European countries. Vet Microbiol 74: 237-248.
3. Vecht U, Wisselink H J, Jellenna M L, Smith H E (1991) Identification of two proteins associated with virulence of *Streptococcus suis* type 2. Infect Immun 59: 3156-3162.
4. Staats J J, Feder I, Okwumabua O, Chengappa M M (1997) *Streptococcus suis*: past and present. Vet Res Commun 21: 381-407.
5. Jacobs A A, Loeffen P L, van den Berg A J, Storm P K (1994) Identification, purification, and characterization of a thiol-activated hemolysin (suilysin) of *Streptococcus suis*. Infect Immun 62: 1742-1748.
6. Wertheim H F, Nghia H D, Taylor W, Schultsz C (2009) *Streptococcus suis*: an emerging human pathogen. Clin Infect Dis 48: 617-625.
7. Ye C, Zhu X, Jing H, Du H, Segura M, et al. (2006) *Streptococcus suis* sequence type 7 outbreak, Sichuan, China. Emerg Infect Dis 12: 1203-1208.
8. Tang J, Wang C, Feng Y, Yang W, Song H, et al. (2006) Streptococcal toxic shock syndrome caused by *Streptococcus suis* serotype 2. PLoS Med 3: e151.
9. Takamatsu D, Wongsawan K, Osaki M, Nishino H, Ishiji T, et al. (2008) *Streptococcus suis* in humans, Thailand. Emerg Infect Dis 14: 181-183.
10. Mai N T, Hoa N T, Nga T V, Linh le D, Chau T T, et al. (2008) *Streptococcus suis* meningitis in adults in Vietnam. Clin Infect Dis 46: 659-667.
11. Swildens B, Nielen M, Wisselink H J, Verheijden J H, Stegeman J A (2007) Elimination of strains of *Streptococcus suis* serotype 2 from the tonsils of carrier sows by combined medication and vaccination. The Veterinary record 160: 619-621.
12. Dekker C N, Bouma A, Daemen A J, van Leengoed L A, Jonker F H, et al. (2012) Homologous whole bacterin vaccination is not able to reduce *Streptococcus suis* serotype 9 strain 7997 transmission among pigs or colonization. Vaccine 30: 1379-1387.
13. Baums C G, Bruggemann C, Kock C, Beineke A, Waldmann K H, et al. (2010) Immunogenicity of an autogenous *Streptococcus suis* bacterin in preparturient sows and their piglets in relation to protection after weaning. Clin Vaccine Immunol 17: 1589-1597.
14. Smith H E, Buijs H, Wisselink H J, Stockhofe-Zurwieden N, Smits M A (2001) Selection of virulence-associated determinants of *Streptococcus suis* serotype 2 by in vivo complementation. Infect Immun 69: 1961-1966.
15. Konings R N, Verhoeven E J, Peeters B P (1987) pKUN, vectors for the separate production of both DNA strands of recombinant plasmids. Methods in enzymology 153: 12-34.
16. Zaccaria E, van Baarlen P, de Greeff A, Morrison D A, Smith H, et al. (2014) Control of competence for DNA transformation in *Streptococcus suis* by genetically transferable pherotypes. PLoS ONE 9: e99394.
17. de Greeff A, Buys H, Verhaar R, Dijkstra J, van Alphen L, et al. (2002) Contribution of fibronectin-binding protein to pathogenesis of *Streptococcus suis* serotype 2. Infect Immun 70: 1319-1325.
18. Ames T D, Rodionov D A, Weinberg Z, Breaker R R (2010) A eubacterial riboswitch class that senses the coenzyme tetrahydrofolate. Chem Biol 17: 681-685.
19. Weinberg Z, Wang J X, Bogue J, Yang J, Corbino K, et al. (2010) Comparative genomics reveals 104 candidate structured RNAs from bacteria, archaea, and their metagenomes. Genome biology 11: R31.
20. Eudes A, Erkens G B, Slotboom D J, Rodionov D A, Naponelli V, et al. (2008) Identification of genes encoding the folate- and thiamine-binding membrane proteins in Firmicutes. J Bacteriol 190: 7591-7594.
21. Xu K, Zhang M, Zhao Q, Yu F, Guo H, et al. (2013) Crystal structure of a folate energy-coupling factor transporter from *Lactobacillus brevis*. Nature 497: 268-271.
22. Lasry I, Berman B, Straussberg R, Sofer Y, Bessler H, et al. (2008) A novel loss-of-function mutation in the proton-coupled folate transporter from a patient with hereditary folate malabsorption reveals that Arg 113 is crucial for function. Blood 112: 2055-2061.
23. de Greeff A, Wisselink Hi, de Bree F M, Schultsz C, Baums C G, et al. (2011) Genetic diversity of *Streptococcus suis* isolates as determined by comparative genome hybridization. BMC Microbiol 11: 161.
24. King Si, Leigh J A, Heath Pi, Luque I, Tarradas C, et al. (2002) Development of a multilocus sequence typing scheme for the pig pathogen *Streptococcus suis*: identification of virulent clones and potential capsular serotype exchange. J Clin Microbiol 40: 3671-3680.
25. Smith H E, Rijnsburger M, Stockhofe-Zurwieden N, Wisselink Hi, Vecht U, et al. (1997) Virulent strains of *Streptococcus suis* serotype 2 and highly virulent strains of *Streptococcus suis* serotype 1 can be recognized by a unique ribotype profile. J Clin Microbiol 35: 1049-1053.

Tables

TABLE 1

Primer sequences.

| Primer name | Sequence 5'-3' | Target |
|---|---|---|
| comE1 | cgagctcggaagaattggttattgcgcgtg | orf2[10]-forward-SacI |
| comE2 | cgggatcccggggatgacctgttgcttg | orf2[10]-reverse-BamHI |
| comE3 | tcccccggggagtcgtgtgtattcgacagcgg | P-orf2-folC[10]-reverse-SmaI |
| comE4 | tcccccggggacaagcaacaggtcatcccc | folC[10]-forward-SmaI |
| comE6 | cgggatcccggttgaatgcccggcaagcc | folC[10]-reverse-BamHI |
| Orf2-fw | ctacggctggttcttctatcgaa | *S. suis* orf2 |
| Orf2-rev | gcaatcggtgtcatgataaagg | *S. suis* orf2 |
| folC-fw | gttttgtccgtccatcggttt | *S. suis* polyfolylpolyglutamate synthase |
| Folc-rev | ctggtcggtcgcatagatga | *S. suis* polyfolylpolyglutamate synthase |
| RecA-fw | ggttttgcaggctcgtatgatg | *S. suis* recombinase A |
| RecA-rev | accaaacatgacaccgactttt | *S. suis* recombinase A |
| t488a | gaaaggtatagtttttagcaag tggacaaaatatatag tgtgtgatacaat | Promoter orf2 |
| t488a_anti | attgtatcacacactatatattttgt ccacttgctaaaaa | Promoter orf2 |
| sense | ctataccttttc | pKUN-V[10]*-SpecR |
| V735-fw | tatgcgcaatgacgtagtagaagg | pKUN-V[10]*-SpecR |
| M13-rev | aacagctatgaccatg | |

TABLE 2

Virulence of complemented *S. suis* strains in germfree piglets; all strains contained a plasmid (pCOM1) with or without insert. V[10]/V[S735]: original 3 kb fragment from strain 10 or strain S735 that was selected from library; orf2[10]: orf2 from V[10]; folC[10]: orf3 from V[10]encoding dihydrofolate synthase.

| Strain | No. of pigs | Dose (CFU) | Mortality[a] (%) | Mean no. of days till death | Morbidity[b] (%) | Clinical index of the group | | | No. of pigs in which *S. suis* was isolated from | | |
|---|---|---|---|---|---|---|---|---|---|---|---|
| | | | | | | Specific[c] symptoms | Non-specific[d] symptoms | Fever index[e] | CNS | Serosae[g] | Joints |
| S735-pCOM1-V[10] | 4 | 10[6] | 100 | 1 | 100 | 100** | 100** | 38* | 4 | 4 | 4 |
| S735-pCOM1-orf2[10] | 4 | 10[6] | 100 | 1 | 100 | 100** | 66** | 29 | 4 | 4 | 4 |
| S735-pCOM1-folC[10] | 4 | 10[6] | 0 | 11 | 0 | 4 | 21 | 1 | 0 | 0 | 0 |
| S735-pCOM1 | 4 | 10[6] | 0 | 11 | 0 | 0 | 21 | 5 | 0 | 0 | 0 |
| S735-pCOM1-V[10]f | 5 | 10[6] | 100 | 1 | 100 | 100** | 100** | 60* | 5 | 5 | 5 |
| S735-pCOM1-V[S735]f | 5 | 10[6] | 20 | 15 | 100 | 43** | 38 | 25 | 1 | 1 | 1 |
| S735-pCOM1[f] | 5 | 10[6] | 20 | 16 | 60 | 14 | 11 | 12 | 1 | 0 | 0 |

TABLE 2-continued

Virulence of complemented *S. suis* strains in germfree piglets; all strains contained a plasmid (pCOM1) with or without insert. V[10]/V[S735]: original 3 kb fragment from strain 10 or strain S735 that was selected from library; orf2[10]: orf2 from V[10]; folC[10]: orf3 from V[10]encoding dihydrofolate synthase.

| Strain | No. of pigs | Dose (CFU) | Mortality[a] (%) | Mean no. of days till death | Morbidity[b] (%) | Clinical index of the group Specific[c] symptoms | Non-specific[d] symptoms | Fever index[e] | No. of pigs in which *S. suis* was isolated from CNS | Serosae[g] | Joints |
|---|---|---|---|---|---|---|---|---|---|---|---|
| T15-pCOM1-V[10] | 5 | $10^6$ | 0 | 14 | 16 | 4 | 16 | 13 | 1 | 1 | 1 |

[a]Percentage of pigs that died due to infection or had to be killed for animal welfare reasons
[b]Percentage of pigs with specific symptoms
[c]Percentage of observations for the experimental group in which specific symptoms (ataxia, lameness of a least one joint and/or stillness) were observed
[d]Percentage of observations for the experimental group in which non-specific symptoms (inappetite and/or depression) were observed
[e]Percentage of observations for the experimental group of a body temperature of >40° C.
[f]Previous experiments (Smith et al., 2001) were re-analyzed to allow for statistical comparison between experiments, this re-analysis required new stringent definitions of specific and aspecific symptoms as indicated in materials and methods.
*$p \leq 0.05$ compared to S735-pCOM1
**$p \leq 0.01$ compared to S735-pCOM1
[g]Serosae are defined as peritoneum, pericardium or pleura

TABLE 3

Sequence analysis of the −35 region of the orf2/folC promoter among various *S. suis* isolates and serotypes[1]

| Sero-type | Phenotype MRP[2] | EF[3] | CGH cluster[4] | Clonal | −35 promoter sequence (5'-3') TGGACA | TGGTCA | TTGTCA |
|---|---|---|---|---|---|---|---|
| 1 | − | − | B | 13 | | | 1/1 |
| 1 | S | + | A | 1 | | 4/4 | |
| 2 | − | − | B | 16/29/147 | | 6/6 | |
| 2 | + | − | B | 28 | | 1/1 | |
| 2 | + | * | A | 1 | | 7/7 | |
| 2 | − | * | A | 1 | | 1/1 | |
| 2 | + | + | A | 1 | 9/9 | | |
| 7 | − | − | B | 29/1 | 1/8[5] | 6/8 | 1/8 |
| 9 | − | − | B | 16 | | 2/2 | |
| 9 | * | − | B | 16 | | 6/6 | |
| 9 | + | − | B | 16 | | 1/1 | |

[1]*S. suis* isolates were described in de Greeff et al. [23]
[2]*indicates an higher molecular weight form of MRP; s indicates a lower molecular weight form of MRP
[3]*indicates an higher molecular weight form of EF
[4]All isolates were genotyped using Comparative Genome Hybridization (CGH) [23]
[5]This isolate belongs to clonal complex 1
[6]Number of isolates analysed/number of isolates with the respective −35 promoter sequence

TABLE 4

Clinical parameters of pigs infected with *S. suis*., experiment 1

| Strain | No. of pigs | Dose | Mortality (%) | Mean no. of days until death | Fever Index | WBC Index | Gross Pathology Arthritis | Pleuritis | Pericarditis | Peritonitis |
|---|---|---|---|---|---|---|---|---|---|---|
| 10 | 5 | $1.1 \times 10^6$ | 100 | 2.6 | 47 | 50 | 11/20 | 2/5 | 2/5 | 1/5 |
| 10ΔfolT | 5 | $9.6 \times 10^5$ | 20 | 6.2** | 23[#] | 19* | 2/20 | 1/5 | 1/5 | 0/5 |

*$p \leq 0.05$ compared to 10
**$p \leq 0.01$ compared to 10
[#]$p \leq 0.1$ compared to 10

TABLE 5

Gross-lesions indicating arthritis and peritonitis: % of positive observations in wild type strain 10 and in 10ΔFolT mutant isolate challenged animals; experiment 2

| | 10 | 10ΔFolT |
|---|---|---|
| Joints | 100 | 20 |
| Peritoneum | 80 | 20 |

TABLE 6

Study design (for study using CBS 143192)

| Group | Treatment | ΔfolT2 CFU per dose | Vaccination (D0, D21) | Challenge (D35) | Off-test |
|---|---|---|---|---|---|
| 1 | Strain 10ΔfolT2 grown in APS media | $5.5 \times 10^7$ CFU | 0.2 mL id | 2 mL ip | D42 |
| 2 | Strain 10ΔfolT2 grown in THB media | $1.4 \times 10^8$ CFU | 0.2 mL id | | |
| 3 | Strain 10ΔfolT2 grown in THB media | $1.4 \times 10^8$ CFU | 2.0 mL im | | |

TABLE 6-continued

Study design (for study using CBS 143192)

| Group | Treatment | ΔfolT2 CFU per dose | Vaccination (D0, D21) | Challenge (D35) | Off-test |
|---|---|---|---|---|---|
| 4 | Placebo vaccine [Negative Control] | N/A | 2.0 mL im | | |
| 5 | No treatment [Strict Control] | N/A | N/A | N/A | |

TABLE 7

Vaccine and placebo preparation (for study using CBS 143192)

| Group | Treatment | Description |
|---|---|---|
| 1 | Strain 10ΔfolT2 grown in APS media | On the vaccination day, ACES-buffered Becton Dickinson APS-TSB media (APS; w/o serum) was inoculated with ΔfolT2 glycerol stock and grown with agitation until 0.6 ± 0.1 OD A600nm. The culture was centrifuged at 9,000 × g for 5 minutes at 4° C. The supernatant was decanted and then the cells were washed twice in an equal volume of sterile 1X PBS, pH 7.2. The washed cells were suspended in PBS to an OD A600nm equal to approximately 9log per mL. Approximately 10 ml of the 9log washed culture was bottled in sterile vials. Aliquots of the treatment were tested for CFU count prior to vaccination and immediately following vaccination. The vaccine preparations were held on wet ice until administration, no longer than 60 minutes. |
| 2, 3 | Strain 10ΔfolT2 grown in THB media | On the vaccination day, Todd Hewitt broth (THB; w/o serum) was inoculated with ΔFolT2 glycerol stock and grown with agitation until 0.6 ± 0.1 OD A600nm. The culture was centrifuged at 9,000 × g for 5 minutes at 4° C. The supernatant was decanted and then the cells were washed twice in an equal volume of sterile 1X PBS, pH 7.2. The washed cells were suspended in PBS to an OD A600nm equal to approximately 9log per mL. Approximately 10 ml of the 9log washed culture was bottled in a sterile vial for the group 2 treatment. An aliquot of the 9log washed culture was further diluted to the target cell concentration in PBS and bottled in a sterile vial for the group 3 treatment. Aliquots of each treatment were tested for CFU count prior to vaccination and immediately following vaccination. The vaccine preparations were held on wet ice until administration, no longer than 60 minutes. |
| 4 | Placebo vaccine | Approximately 40 ml of sterile phosphate buffered saline (PBS), pH 7.2 was bottled in a sterile vial and stored at 4° C. until use. |

TABLE 8

Challenge preparation (for study using CBS 143192)

| Strain Preparation | S. suis type 2 BIAH #08-06 (ATCC 700794 derivative) A single colony was inoculated into 10 mL pre-warmed THB + 5% FBS and grown statically to 0.5 ± 0.1 OD A600nm. The culture was scaled up to 900 mL in THB + 5% FBS, and grown with agitation to 0.7 ± 0.1 OD A600nm. Sterile glycerol was added to the culture (10% v/v). Aliquots were retained for pre-freeze and post-thaw CFU and for purity. The challenge was dispensed into vaccine bottles and stored at −70° C. until use. Prior to use, the culture was thawed in a 37° C. waterbath, then diluted with sterile THB + 5% FBS to meet the target concentration of $1 \times 10^9$ cfu/mL. Aliquots of the treatment were tested for CFU count prior to challenge and immediately following challenge. |
|---|---|

TABLE 9

Percentage of animals that died or were euthanized following challenge (mortality) (for study using CBS 143192)

| Group | # Pigs challenged | Vaccine | Mortality |
|---|---|---|---|
| 1 | 14 | Strain 10ΔfolT2-7log-APS-id | 35.7% |
| 2 | 11 | Strain 10ΔfolT2-8log-THB-id | 45.5% |
| 3 | 11 | Strain 10ΔfolT2-8log-THB-im | 27.3% |
| 4 | 15 | Placebo vaccine-Negative Control | 93.3% |

TABLE 10

Percentage of animals showing severe lameness following challenge (for study using CBS 143192)

| Group | # Pigs challenged | Vaccine | Percentage of pigs showing severe lameness during observation period |
|---|---|---|---|
| 1 | 14 | Strain 10ΔfolT2-7log-APS-id | 4.2% |
| 2 | 11 | Strain 10ΔfolT2-8log-THB-id | 0% |
| 3 | 11 | Strain 10ΔfolT2-8log-THB-im | 3.3% |
| 4 | 15 | Placebo vaccine-Negative Control | 41.7% |

TABLE 11

Percentage of animals showing apathy following challenge (for study using CBS 143192)

| Group | # Pigs challenged | Vaccine | Percentage of pigs showing apathy during observation period |
|---|---|---|---|
| 1 | 14 | Strain 10ΔfolT2-7log-APS-id | 21.1% |
| 2 | 11 | Strain 10ΔfolT2-8log-THB-id | 4.3% |
| 3 | 11 | Strain 10ΔfolT2-8log-THB-im | 11.7% |
| 4 | 15 | Placebo vaccine-Negative Control | 50.0% |

TABLE 12

Percentage of animals showing signs of inflammation in brain during necropsy (for study using CBS 143192)

| Group | # Pigs challenged | Vaccine | Percentage of pigs showing inflammation in brain |
|---|---|---|---|
| 1 | 14 | Strain 10ΔfolT2-7log-APS-id | 21% |
| 2 | 11 | Strain 10ΔfolT2-8log-THB-id | 45% |
| 3 | 11 | Strain 10ΔfolT2-8log-THB-im | 27% |
| 4 | 15 | Placebo vaccine-Negative Control | 87% |

TABLE 13

Percentage of animals from which S. suis was recovered from brain swabs collected at necropsy (for study using CBS 143192)

| Group | # Pigs challenged | Vaccine | Percentage of pigs from which S. suis was recovered from brain |
|---|---|---|---|
| 1 | 14 | Strain 10ΔfolT2-7log-APS-id | 35.7% |
| 2 | 11 | Strain 10ΔfolT2-8log-THB-id | 27.3% |
| 3 | 11 | Strain 10ΔfolT2-8log-THB-im | 27.3% |
| 4 | 15 | Placebo vaccine-Negative Control | 93.3% |

TABLE 14

Percentage of animals from which S. suis was recovered from the joints swabs collected at necropsy (for study using CBS 143192)

| Group | # Pigs challenged | Vaccine | Percentage of pigs from which S. suis was recovered from the joints |
|---|---|---|---|
| 1 | 14 | Strain 10ΔfolT2-7log-APS-id | 35.7% |
| 2 | 11 | Strain 10ΔfolT2-8log-THB-id | 36.4% |
| 3 | 11 | Strain 10ΔfolT2-8log-THB-im | 18.2% |
| 4 | 15 | Placebo vaccine-Negative Control | 73.3% |

TABLE 15

Vaccination challenge study outline (for study using CBS 140425)

| Group | # Pigs | Treatment | Inclusion Level/2 ml dose | Days of Treatment | Vacc. Route | Challenge Day | Chall. Route |
|---|---|---|---|---|---|---|---|
| 1 | 15 | Strain 10ΔfolT | $1.0 \times 10^{10}$ CFU (first vac) $9.8 \times 10^{9}$ CFU (second vac) | 0, 21 | i.m. | 36 | i.p. |
| 2 | 15 | Strain 10ΔfolT | $9.5 \times 10^{9}$ CFU | 0 | i.m. | 36 | i.p. |
| 3 | 15 | Placebo [Negative Control] | N/A | 0, 21 | i.m. | 36 | i.p. |
| 4 | 5 | Strict control | N/A | N/A | N/A | N/A | N/A |

TABLE 16

Vaccine preparation (for study using CBS 140425)

| Group | Treatment | Description |
|---|---|---|
| 1-2 | Strain 10ΔfolT | A strain 10ΔfolT glycerol stock was transferred into Todd-Hewitt Broth (THB) + 5% Fetal Bovine Serum (FBS) and grown statically to 0.5 ± 0.1 OD A600nm. The culture was scaled up to 1800 mL in THB + 5% FBS, and grown with agitation to 0.7 ± 0.1 OD A600nm. The culture was concentrated 6X by centrifugation and removal of supernatant to achieve a 10-log dose. Sterile glycerol was added to the concentrated culture |

TABLE 16-continued

Vaccine preparation (for study using CBS 140425)

| Group | Treatment | Description |
|---|---|---|
| | | (10% v/v). Aliquots were retained for pre-freeze and post-thaw CFU, identity, and purity. The vaccine was dispensed into vaccine bottles and stored at −70° C. until use. The vaccine was thawed in a 37° C. water bath and diluted to the intended target concentration using storage media, then held on wet ice until administration. |
| 6 | Placebo | Sterile THB + 5% FBS media, stored at 4° C. until use. |

TABLE 17

Challenge preparation (for study using CBS 140425)

| Challenge Strain | S. suis type 2 BIAH #08-06 (ATCC 700794 derivative) |
|---|---|
| Challenge Preparation | A single colony was inoculated into 20 mL pre-warmed THB + 5%FBS and grown statically to 0.5 ± 0.1 OD A600nm. The culture was scaled up to 900 mL in THB + 5% FBS, and grown with agitation to 0.7 ± 0.1 OD A600nm. Sterile glycerol was added to the culture (10% v/v). Aliquots were retained for pre-freeze and post-thaw CFU and for purity. The challenge was dispensed into vaccine bottles and stored at −70° C. until use. |

TABLE 18

Percentage of animals showing lameness following challenge (CBS 140425)

| Group | # Pigs | Vaccine | Percentage of pigs showing lameness |
|---|---|---|---|
| 1 | 13 | Strain 10ΔfolT-10logs-2 dose | 7.7% |
| 2 | 15 | Strain 10ΔfolT-10logs-1 dose | 40.0% |
| 3 | 15 | Placebo Negative Control | 93.3% |

TABLE 19

Percentage of animals showing abnormal behavior following challenge (CBS 140425)

| Group | # Pigs | Vaccine | Percentage of pigs showing abnormal behavior |
|---|---|---|---|
| 1 | 13 | Strain 10ΔfolT-10logs-2 dose | 0% |
| 2 | 15 | Strain 10ΔfolT-10logs-1 dose | 46.7% |
| 3 | 15 | Placebo Negative Control | 100% |

TABLE 20

Percentage of animals expired or euthanized following challenge (mortality) (CBS 140425)

| Group | # Pigs | Vaccine | Mortality (%) |
|---|---|---|---|
| 1 | 13 | Strain 10ΔfolT-10logs-2 dose | 0% |
| 2 | 15 | Strain 10ΔfolT-10logs-1 dose | 26.7% |
| 3 | 15 | Placebo-Negative Control | 100% |

TABLE 21

Percentage of animals with abnormal findings in brain upon necropsy (CBS 140425)

| Group | # Pigs | Vaccine | Percentage of pigs with abnormal findings in CNS (%) |
|---|---|---|---|
| 1 | 13 | Strain 10ΔfolT-10logs-2 dose | 0% |
| 2 | 15 | Strain 10ΔfolT-10logs-1 dose | 26.7% |
| 3 | 15 | Placebo-Negative Control | 93.3% |

TABLE 22

Percentage of animals with abnormal findings in thoracic cavity upon necropsy (CBS 140425)

| Group | # Pigs | Vaccine | Percentage of pig with lesions in thoracic cavity (%) |
|---|---|---|---|
| 1 | 13 | Strain 10ΔfolT-10logs-2 dose | 23.1% |
| 2 | 15 | Strain 10ΔfolT-10logs-1 dose | 33.3% |
| 3 | 15 | Placebo-Negative Control | 93.3% |

TABLE 23

Percentage of animals from which S. suis was recovered from brain swab (CBS 140425)

| Group | # Pigs | Vaccine | S. suis recovered from CNS swab (%) |
|---|---|---|---|
| 1 | 13 | Strain 10ΔfolT-10logs-2 dose | 0% |
| 2 | 15 | Strain 10ΔfolT-10logs-1 dose | 6.7% |
| 3 | 15 | Placebo-Negative Control | 73.3% |

SEQUENCE LISTING

```
Sequence total quantity: 27
SEQ ID NO: 1         moltype = DNA  length = 30
FEATURE              Location/Qualifiers
misc_feature         1..30
                     note = Primer comE1
```

```
source                  1..30
                        mol_type = other DNA
                        organism = synthetic construct
SEQUENCE: 1
cgagctcgga agaattggtt attgcgcgtg                                              30

SEQ ID NO: 2            moltype = DNA   length = 29
FEATURE                 Location/Qualifiers
misc_feature            1..29
                        note = Primer comE3
source                  1..29
                        mol_type = other DNA
                        organism = synthetic construct
SEQUENCE: 2
cgggatcccg ggggatgacc tgttgcttg                                               29

SEQ ID NO: 3            moltype = DNA   length = 33
FEATURE                 Location/Qualifiers
misc_feature            1..33
                        note = Primer comE3
source                  1..33
                        mol_type = other DNA
                        organism = synthetic construct
SEQUENCE: 3
tcccccgggg gagtcgtgtg tattcgacag cgg                                          33

SEQ ID NO: 4            moltype = DNA   length = 31
FEATURE                 Location/Qualifiers
misc_feature            1..31
                        note = Primer comE4
source                  1..31
                        mol_type = other DNA
                        organism = synthetic construct
SEQUENCE: 4
tcccccgggg gacaagcaac aggtcatccc c                                            31

SEQ ID NO: 5            moltype = DNA   length = 29
FEATURE                 Location/Qualifiers
misc_feature            1..29
                        note = Primer comE6
source                  1..29
                        mol_type = other DNA
                        organism = synthetic construct
SEQUENCE: 5
cgggatcccg gttgaatgcc cggcaagcc                                               29

SEQ ID NO: 6            moltype = DNA   length = 23
FEATURE                 Location/Qualifiers
misc_feature            1..23
                        note = Primer Orf2-fw
source                  1..23
                        mol_type = other DNA
                        organism = synthetic construct
SEQUENCE: 6
ctacggctgg ttcttctatc gaa                                                     23

SEQ ID NO: 7            moltype = DNA   length = 22
FEATURE                 Location/Qualifiers
misc_feature            1..22
                        note = Primer Orf2-rev
source                  1..22
                        mol_type = other DNA
                        organism = synthetic construct
SEQUENCE: 7
gcaatcggtg tcatgataaa gg                                                      22

SEQ ID NO: 8            moltype = DNA   length = 20
FEATURE                 Location/Qualifiers
misc_feature            1..20
                        note = Primer folC-fw
source                  1..20
                        mol_type = other DNA
                        organism = synthetic construct
SEQUENCE: 8
gtttgtccgt ccatcggttt                                                         20

SEQ ID NO: 9            moltype = DNA   length = 20
FEATURE                 Location/Qualifiers
misc_feature            1..20
```

```
                            note = Primer folC-rev
source                      1..20
                            mol_type = other DNA
                            organism = synthetic construct
SEQUENCE: 9
ctggtcggtc gcatagatga                                                20

SEQ ID NO: 10               moltype = DNA  length = 21
FEATURE                     Location/Qualifiers
misc_feature                1..21
                            note = Primer RecA-fw
source                      1..21
                            mol_type = other DNA
                            organism = synthetic construct
SEQUENCE: 10
ggtttgcagg ctcgtatgat g                                              21

SEQ ID NO: 11               moltype = DNA  length = 23
FEATURE                     Location/Qualifiers
misc_feature                1..23
                            note = Primer RecA-rev
source                      1..23
                            mol_type = other DNA
                            organism = synthetic construct
SEQUENCE: 11
accaaacatg acaccgactt ttt                                            23

SEQ ID NO: 12               moltype = DNA  length = 51
FEATURE                     Location/Qualifiers
misc_feature                1..51
                            note = Primer t488a
source                      1..51
                            mol_type = other DNA
                            organism = synthetic construct
SEQUENCE: 12
gaaaggtata gttttagca agtggacaaa atatatagtg tgtgatacaa t              51

SEQ ID NO: 13               moltype = DNA  length = 51
FEATURE                     Location/Qualifiers
misc_feature                1..51
                            note = Primer t488a_antisense
source                      1..51
                            mol_type = other DNA
                            organism = synthetic construct
SEQUENCE: 13
attgtatcac acactatata ttttgtccac ttgctaaaaa ctataccttt c              51

SEQ ID NO: 14               moltype = DNA  length = 24
FEATURE                     Location/Qualifiers
misc_feature                1..24
                            note = Primer V735-fw
source                      1..24
                            mol_type = other DNA
                            organism = synthetic construct
SEQUENCE: 14
tatgcgcaat gacgtagtag aagg                                           24

SEQ ID NO: 15               moltype = DNA  length = 16
FEATURE                     Location/Qualifiers
misc_feature                1..16
                            note = Primer M13-rev
source                      1..16
                            mol_type = other DNA
                            organism = synthetic construct
SEQUENCE: 15
aacagctatg accatg                                                    16

SEQ ID NO: 16               moltype = AA  length = 5
FEATURE                     Location/Qualifiers
source                      1..5
                            mol_type = protein
                            organism = Streptococcus suis
SEQUENCE: 16
FYRKP                                                                5

SEQ ID NO: 17               moltype = AA  length = 168
FEATURE                     Location/Qualifiers
source                      1..168
                            mol_type = protein
```

```
                          organism = Clostridium bolteae
SEQUENCE: 17
MTKTKHMVWM GILIAVSIVL SRFLSFSAWN VKIGFAFIPI VIGAVLFGPV QGGIAAAAAD    60
FLGAILFPIG MYFPGFTVTA FLTGLTYGIL LHKNRSMFRI ACAVLIVQLV YGLLLNTCWI   120
SLLYGAPYLA LLSTRIVQYV VLIPVQFVII ARMYVLGSKK YHILQENS                168

SEQ ID NO: 18           moltype = AA   length = 187
FEATURE                 Location/Qualifiers
source                  1..187
                        mol_type = protein
                        organism = Clostridium phytofermentans
SEQUENCE: 18
MLNQEKNVKN KDLKKGKKVF TLETFIVLAL LVAIEVILTR FLSLKEWNIR FSFGFIPVVI    60
AAILYGPIAS ATVAACSDFL GAILFPMGAY FPGFTITAFI SGIVYGLFLH KKQSLPNIVG   120
AAVVNQFFCG LVINSYWLSI ISGKSTFWGL IPIRSIQSAV MSIVIISVTY VISKTIVPII   180
KKAIVIM                                                             187

SEQ ID NO: 19           moltype = AA   length = 189
FEATURE                 Location/Qualifiers
source                  1..189
                        mol_type = protein
                        organism = unidentified
                        note = Alkaliphilus metalliredigens
SEQUENCE: 19
MKFNTRKLVT LSLLMALTIV FTRIASIRIP FGGVEGVRVG FGSLPILLAG ILFGPISGFI    60
VGALGDLIGY FLNPMGAYMP HFTLSAGLSG FIPGSIYYFT FRPKSNIHFS SKLQVSRPSF   120
WLIFISILIG QVTISLLLIP YFLSALFSIP YELTIIPRTI TQLISIPIFS WVIWIISNKT   180
NIFDYVKSK                                                           189

SEQ ID NO: 20           moltype = AA   length = 162
FEATURE                 Location/Qualifiers
source                  1..162
                        mol_type = protein
                        organism = Caldanaerobacter subterraneus
                        note = Thermoanaerobacter tengcongensis
SEQUENCE: 20
MKKFTTREIA FLALLVALNI VLTRIASIRI AIGGVEGIRI GFGAFPVIFS GIAFGPYAGG    60
IVGALGDIIG YFINPMGPYM PHFTFTAALV GILPPLFLKP FKAQIPTFWQ LVIAIGLGQT   120
ISSIILTPYF IQMLFHLPMK ITVPPRIVTQ AIQVPLYAFL LK                      162

SEQ ID NO: 21           moltype = AA   length = 175
FEATURE                 Location/Qualifiers
source                  1..175
                        mol_type = protein
                        organism = Enterococcus faecium
SEQUENCE: 21
HRLDARMIAI MGLLIALMVT LSRLVAIETP FIKISVTFIP QVIMGILFGP FWSGIGAVLA    60
DLVGMALFSK SAFFIGFTLN AFIEGAIYGF FFYRKEITWK NAILATLSVT LIINLFLTPL   120
WLALMYHVPL FSWVVWAPRL LKTVIWLPIQ SIAIYYVGRS IPYKKILRSL AIHAK         175

SEQ ID NO: 22           moltype = AA   length = 179
FEATURE                 Location/Qualifiers
source                  1..179
                        mol_type = protein
                        organism = Enterococcus faecalis
SEQUENCE: 22
MTKKKFGTKS IALMGVLIAV VVVFSRFFAY ETTFLKISFT FIPESLIGMI FGPFWAGIGT    60
AVADVVGMLL FPKAGYFPGF TLNAFLAGAI YGYFYYKKEM TWQRVILATL LVTVLINIIL   120
TPLWLSLMYG VNLANFAWWV PRLIKTVIFF PIQVIATYYL GNKIPFKRLF GKPLSELDQ    179

SEQ ID NO: 23           moltype = AA   length = 177
FEATURE                 Location/Qualifiers
source                  1..177
                        mol_type = protein
                        organism = Lactobacillus brevis
SEQUENCE: 23
MKTMAKTQLP KLDTLSMVTM GVLMALQLVI SRFSVGNNFI KVSFTFLIVA LIAKWFGPWW    60
GMLTAAVVDV IGTLMTGGPF FIGFTVSAVL GSLIYAVPLY RQPVSWWRVI GASVLIALLV   120
NTLLNTLWVT IMYQTPFWSL LPVRALKELI VTPVQILVLY LLLKSQVIQM IQARLNK      177

SEQ ID NO: 24           moltype = AA   length = 186
FEATURE                 Location/Qualifiers
source                  1..186
                        mol_type = protein
                        organism = Streptococcus mutans
SEQUENCE: 24
MNTMFKSPKL SPQRLVTLAM LIALAFAIGK FSIPIIPQQL IISPTFIVNV MIGMIGGPIW    60
AFISLAILDI VDNLSSGAGN FIIWTLLEA  VQGLFYGLFF YQKSLSWTNK KDWLHVTIAT   120
AIIMLIGSFI FTPLLVQIYY GVPFWAQFAA GRWLKIFEIP IRILVTMAIM PQLQRIPELR   180
```

-continued

```
KLANFK                                                            186

SEQ ID NO: 25           moltype = AA  length = 186
FEATURE                 Location/Qualifiers
source                  1..186
                        mol_type = protein
                        organism = Streptococcus gallolyticus
SEQUENCE: 25
MNLFFKTPKL TLKRLVSLAM LIALAFIVGK FSIPVIPQQL VVSLTFIVNT IIGMIGGPIW  60
GFISLGILDV VDTLSSSSAG NFIIWWTLME AIQGFFYGLF FYGKPLSWSS KKDWLHVTIA  120
TVVIMLIGTF ILTPLLIQIY FGVPFWAQYL AGRWLKIFEI PLRIIITMLV IPRLQKIPEL  180
RKLANL                                                            186

SEQ ID NO: 26           moltype = AA  length = 185
FEATURE                 Location/Qualifiers
source                  1..185
                        mol_type = protein
                        organism = Streptococcus uberis
SEQUENCE: 26
MPKQLYFPKL TVQRLVTLAM LIALAVIVSK FSVSIIPNQL VISFTFIVNT VIGIIAGPFW  60
SFITLAMIDL IDSLMGGTSH FIIWWTVMEA FQGLLYGFFF YKRPLRSNQK KDWIYVSAVT  120
LVIMLFSTFL ITPLLIQIYF HVPFWAQYAA GRWFKIFEIP LRVLLTMFLI PPLQRIPEIK  180
KLSAL                                                             185

SEQ ID NO: 27           moltype = AA  length = 183
FEATURE                 Location/Qualifiers
source                  1..183
                        mol_type = protein
                        organism = Streptococcus suis
SEQUENCE: 27
MEKKIPKLTV QLLAAIAMTL ALVMIVENYF SIRISDTLQV QFTFIPNTIL GAIAGPVWAA  60
VFAAISDPVF VLFSGQTVLF TWILIEAVSA FIYGWFFYRK PLDTKNKADW LYVAGVVVLI  120
QVVISFIMTP IALHFHFGTP WIVLYSSRLI KAVFEIPLRI VVTMLVLPSL QKIPELAKLM  180
GIK                                                               183
```

The invention claimed is:

1. A method to reduce virulence of a *Streptococcus suis* (*S. suis*) bacterium comprising reducing the capacity of said bacterium to transport folate compared to wild type; wherein said capacity has been reduced by deletion or inactivation of a gene of the *S. suis* encoding folate transporter (FolT) function.

2. A method according to claim 1 wherein said bacterium is capable of de novo folate synthesis.

3. A method according to claim 1 comprising attenuating expression and/or function of the folate substrate binding protein (FolT) of said bacterium.

4. A method according to claim 1 wherein said virulence is attenuated by providing a mutation, deletion or insertion in the foltT gene of said bacterium.

5. A method according to claim 4 wherein said virulence is attenuated by providing a mutation, deletion or insertion in the DNA of said bacterium encoding the promotor of the folT gene.

6. A method according to claim 4 wherein said virulence is attenuated by providing a mutation, deletion or insertion in the DNA of said bacterium encoding a transmembrane region of folate substrate binding protein FolT.

7. A method according to claim 4 wherein said virulence is attenuated by providing a mutation, deletion or insertion in the FolT encoding DNA region of said bacterium encoding a region crucial for substrate binding.

8. A method according to claim 1 wherein said bacterium is a Firmicutes, preferably a *Streptococcus*, more preferably a *Streptococcus suis*, more preferably a ΔFolT mutant deposited as "CBS 140425 *Streptococcus suis* ΔFolT mutant" at the Centraalbureau voor Schimmelcultures at Aug. 19, 2015, most preferably a ΔFolT mutant deposited as "CBS 143192 *Streptococcus suis* ΔFolT2 mutant" at the Westerdijk Fungal Biodiversity Institute at Aug. 25, 2017.

9. A bacterium with attenuated virulence obtainable or obtained with a method according to claim 1.

10. A method of treating *Streptococcus* infection in swine comprising administering a composition comprising a recombinant ΔFolT mutant of a *Streptococcus suis* (*S. suis*) bacterium having reduced capacity to transport folate compared to wild type, wherein said capacity has been reduced by deletion or inactivation of a gene of the *S. suis* encoding folate transporter (FolT) function.

11. The method of treating *Streptococcus* infection in swine of claim 10, wherein the composition comprising the recombinant ΔFolT mutant bacterium is administered intravenously.

12. The method of claim 11, wherein the recombinant ΔFolT mutant bacterium is present in an amount of about $9\times10^5$ CFU to $1.5\times10^7$ CFU.

13. The method of claim 12, wherein the recombinant ΔFolT mutant bacterium is present in an amount of $9\times10^5$ CFU.

14. The method of claim 12, wherein the recombinant ΔFolT mutant bacterium is present in an amount of $1.5\times10^7$ CFU.

* * * * *